United States Patent [19]

Naito et al.

[11] 4,198,504
[45] Apr. 15, 1980

[54] [3-(PYRIDINIUM)-7-(NAPHTHYIRIDINYL CARBONYLAMINO)ACETAMIDO]CEPHALOSPORANIC ACID DERIVATIVES

[75] Inventors: Takayuki Naito, Kawasaki; Jun Okumura; Masahisa Oka, both of Yokohama, all of Japan

[73] Assignee: Bristol-Myers Company, New York, N.Y.

[21] Appl. No.: 957,113

[22] Filed: Nov. 2, 1978

[51] Int. Cl.$^2$ ............................................ C07D 501/46
[52] U.S. Cl. ............................................................ 544/25
[58] Field of Search ........................................ 544/25

[56] References Cited

U.S. PATENT DOCUMENTS

| | | | |
|---|---|---|---|
| 3,207,755 | 7/1960 | Abraham et al. | 260/243 |
| 3,217,000 | 11/1965 | Flynn | 260/243 |
| 3,219,662 | 4/1962 | Abraham et al. | 260/243 |
| 3,222,362 | 12/1965 | Flynn | 260/243 C |
| 3,222,363 | 12/1965 | Flynn | 260/243 |
| 3,225,038 | 12/1965 | Flynn | 260/243 |
| 3,226,384 | 12/1965 | Abraham et al. | 260/243 |
| 3,270,009 | 8/1966 | Flynn | 260/243 |
| 3,270,012 | 8/1966 | Higgins | 260/243 |
| 3,280,118 | 10/1966 | Eardley et al. | 260/243 C |
| 3,449,338 | 6/1969 | Flynn | 260/243 C |
| 3,479,350 | 11/1969 | Eardley et al. | 260/243 C |
| 3,483,197 | 12/1969 | Bickel et al. | 260/243 |
| 3,557,104 | 1/1971 | Bickel et al. | 260/243 |
| 3,632,810 | 1/1972 | Bickel et al. | 260/243 C |
| 3,775,410 | 11/1973 | Christensen et al. | 260/243 C |
| 3,790,565 | 2/1974 | Vanevenhoven | 260/243 C |
| 3,792,047 | 2/1974 | Arkley et al. | 260/243 C |
| 3,945,995 | 3/1976 | Yamada et al. | 260/239.1 |
| 3,985,742 | 10/1976 | Stapley et al. | 260/243 C |
| 4,015,000 | 3/1977 | Kocsis et al. | 544/25 |
| 4,017,487 | 4/1977 | Stapley et al. | 260/243 C |
| 4,024,134 | 5/1977 | Gregson et al. | 260/243 C |
| 4,041,161 | 8/1977 | Kocsis et al. | 544/25 |
| 4,061,748 | 12/1977 | Yamada et al. | 424/246 |
| 4,074,047 | 2/1978 | Foxton et al. | 544/30 |
| 4,138,554 | 2/1979 | Naito et al. | 544/22 |

FOREIGN PATENT DOCUMENTS

| | | | |
|---|---|---|---|
| 2520561 | 11/1975 | Fed. Rep. of Germany | 544/22 |
| 2614303 | 10/1976 | Fed. Rep. of Germany | 544/30 |
| 50-33824 | 3/1975 | Japan . | |
| 50-23827 | 12/1975 | Japan . | |
| 51-41011 | 8/1976 | Japan . | |
| 52-105244 | 3/1977 | Japan . | |
| 52-23485 | 7/1977 | Japan . | |
| 1522140 | 12/1974 | United Kingdom . | |

OTHER PUBLICATIONS

Spencer, "Antimicrobial Agents & Chemotherapy", (1966) p. 573ff.

*Primary Examiner*—David Wheeler
*Attorney, Agent, or Firm*—H. W. Taylor, Jr.

[57] ABSTRACT

7-[α-(4-hydroxy-1,5-naphthyridine-3-carboxamido)-α-phenyl or thienyl (and substituted phenyl) acetamido]-3-(pyridiniummethyl)-3-cephem-4-carboxylates having on the pyridine ring an acidic group which is preferably —COOH or —SO$_3$H and also, if desired, having one or two methylene groups together with or without a hetero atom between the pyridine ring and the acidic group were synthesized and found to have potent antibacterial activity in vitro especially against many strains of *Pseudomonas aeruginosa* and also high solubility in water.

62 Claims, No Drawings

[3-(PYRIDINIUM)-7-(NAPHTHYIRIDINYL CARBONYLAMINO)ACETAMIDO]CEPHALOSPORANIC ACID DERIVATIVES

BACKGROUND OF THE INVENTION

1. Field of the Invention

The chemical compounds of the present invention belong to the class of antibacterial agents commonly called cephalosporins.

2. Description of the Prior Art

The preparation of pyridine derivatives (betaines or 3-pyridiniummethyl compounds) of cephalosporins began with such derivatives of cephalosporin C itself which were called the cephalosporin $C_A$ family. (See Biochemical J., 79, 403–408 (1961); U.S. Pat. Nos. 3,207,755; 3,219,662 and 3,226,384). Next came cephaloridine produced in that manner from cephalothin and also betaine derivatives of other 7-acylaminocephalosporanic acids; see Antimicrobial Agents and Chemotherapy, 573–580 (1967) in which the pyridine ring also contained substituents which were primarily alkyl or carboxamido groups but also included 3-COOH, 4-COOH (i.e., from nicotinic acids), 3-CH$_2$COOH and 3-SO$_3$H as well as halogens, nitriles etc. See also U.S. Pat. No. 3,449,338 in which claim 1 reads as follows:

"1. The compounds having the following formula:

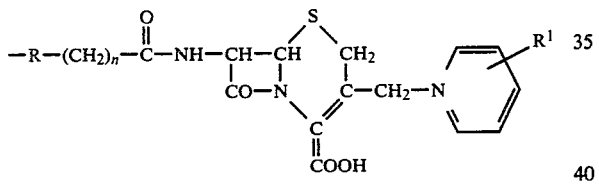

wherein R is a member of the group consisting of α-thienyl, β-thienyl, α-furyl, and β-furyl; n is 0 or 1; $R^1$ is a member of the group consisting of hydrogen, methyl, ethyl, hydroxy, hydroxymethyl, trifluoromethyl, halo, cyano, carboxy, carbo(C$_1$–C$_4$)alkoxy, (C$_1$–C$_4$) alkanoyl, (C$_1$–C$_4$)alkanoyloxy, and

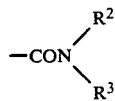

attached to the pyridine ring in the 3 and 4 positions; $R^2$ is a member of the group consisting of hydrogen, methyl, ethyl, and cyclopropyl; and $R^3$ is a member of the group consisting of hydrogen, methyl, and ethyl."
See also U.S. Pat. Nos. 3,280,118 and 3,479,350 and U.K. Pat. No. 1,522,140.

Subsequent use primarily of pyridine and isonicotinamide is reflected in many patents in which there is generic disclosure having about the same breadth as that of U.S. Pat. No. 3,449,338 but containing no working examples or other details, as of preparation and properties, for any other compounds. Examples of early patents of this type are U.S. Pat. No. 3,217,000 (as well as U.S. Pat. Nos. 3,222,362; 3,222,363; 3,270,009 and 3,225,038) and 3,270,012 (see column 3).

Later such unsupported generalities appear, for example, in U.S. Pat. Nos. 3,483,197; 3,557,104; 3,632,810; 3,985,742 (see column 83); 4,024,134; 4,041,161 and 4,074,047. And see Derwent 23827A.

The hydroxylmethyl substituent is shown in U.S. Pat. No. 3,792,047. U.S. Pat. No. 3,790,565 reviews the literature.

In the 7-methoxy series of cephamycins see, for example, the listing in column 83 of U.S. Pat. No. 4,017,487 and column 3 of U.S. Pat. No. 3,775,410.

Sodium 7-[D-α-(4-hydroxy-1,5-naphthyridine-3-carboxamido)-α-phenylacetamido]-3-acetoxymethyl-3-cephem-4-carboxylate is described in Farmdoc (Derwent) abstract 65042X and see also Farmdoc 26113Y, 47004Y and 20763X and U.S. Pat. No. 4,061,748.

U.S. Pat. No. 3,945,995 describes the preparation of the N-hydroxysuccinimido ester of 4-hydroxy-1,5-naphthyridine-3-carboxyic acid.

As disclosed in our prior, copending U.S. application Ser. No. 874,456 filed Feb. 2, 1978 we have previously prepared the following compounds:

- 7-[D-α-(4-hydroxy-1,5-naphthyridine-3-carboxamido)-α-phenylacetamido]-3-(4-carbamoyl-pyridinium)-methyl-3-cephem-4-carboxylate;
- 7-[D-α-(4-hydroxy-1,5-naphthyridine-3-carboxamido)-α-(4-hydroxyphenyl)acetamido[-3-(4-carbamoyl-pyridinium)methyl-3-cephem-4-carboxylate;
- 7-[D-α-(4-hydroxy-1,5-naphthyridine-3-carboxamido)-α-(3,4-dihydroxyphenyl)acetamido]-3-(4-carbamoylpyridinium)methyl-3-cephem-4-carboxylate;
- 7-[D-α-(4-hydroxy-1,5-naphthyridine-3-carboxamido)-α-(3-chloro-4-hydroxyphenyl)acetamido]-3-(4-carbamoylpyridinium)methyl-3-cephem-4-carboxylate;
- 7-[D-α(4-hydroxy-1,5-naphthyridine-3-carboxamido)-α-(3-thienyl)acetamido]-3-(4-carbamoyl-pyridinium)-methyl-3-cephem-4-carboxylate.

These compounds were found to be potent antibacterial agents but all of them had a solubility in water of less than 5 mgm./ml. This unfortunate characteristic renders them unsuitable for use by intravenous administration. Acceptable solubility for such use is at least 125 mgm./ml. so that 250 mgm. can be administered in 2 ml. of sterile solution. Suspensions cannot, of course, be administered intravenously. It was the object of the present invention to provide potent antibacterial agents, especially against *Pseudomonas aeruginosa*, having a solubility in water greater than 125 mgm./ml. and preferably of at least 250 mgm./ml. The latter would make possible a dosage of 500 mgm. in a 2 ml. vial.

SUMMARY OF THE INVENTION

There is provided by the present invention the compounds having the D configuration in the 7-sidechain and the formula

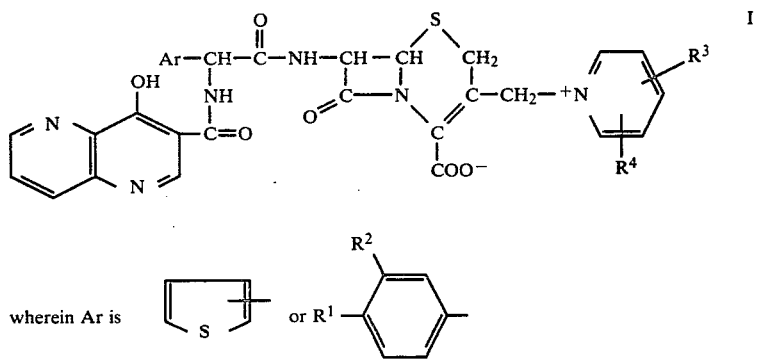

wherein Ar is 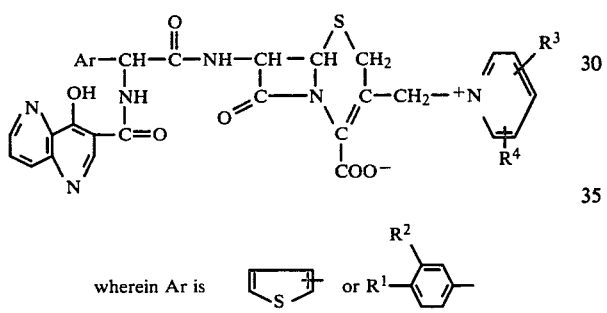

wherein $R^1$ is hydrogen or hydroxy and $R^2$ is hydrogen, hydroxy, methyl, methoxy or chloro and $R^3$ is hydrogen and $R^4$ is carboxyl, carboxymethyl, —$SO_3H$, —$CH_2CH_2COOH$, —CH=CHCOOH, —$CH_2CH_2SO_3H$, —$SCH_2COOH$ or $R^3$ and $R^4$ are each carboxyl substituted at the 2,3-, 2,4-, 2,5-, 2,6-, 3,4- or 3,5-positions or an alkali metal salt thereof.

Preferred compounds of the present invention are the compounds having the D configuration in the 7-side-chain and the formula wherein Ar is wherein $R^1$ is hydrogen or hydroxy and $R^2$ is hydrogen, hydroxy, methyl, methoxy or chloro and $R^3$ is hydrogen and $R^4$ is carboxyl, carboxymethyl, 3- or 4-$SO_3H$, 3- or 4-$CH_2CH_2COOH$, 3- or 4-CH=CHCOOH, 3- or 4-$CH_2CH_2SO_3H$ or 3- or 4-$SCH_2COOH$ or $R^3$ and $R^4$ are each carboxyl substituted at the 2,3-, 2,4-, 2,5-, 2,6-, 3,4- or 3,5-positions or an alkali metal salt thereof; particularly preferred compounds in this series are those in which Ar is phenyl, $R^1$ is hydroxy and $R^2$ is hydrogen, chloro or hydroxy.

Other preferred compounds of the present invention are those of formula I in which $R^1$ and $R^2$ are hydrogen or $R^1$ is hydroxy and $R^2$ is hydrogen, chloro or hydroxy.

Preferred species of the present invention are the following compounds:

7-[D-α-(4-hydroxy-1,5-naphthyridine-3-carbox-amido)-α-phenylacetamido]-3-(4′-carboxypyridinium)-methyl-3-cephem-4-carboxylate; 7-[D-α-(4-hydroxy-1,5-naphthyridine-3-carboxamido)-α-(4-hydroxyphenyl)acetamido]-3-(4′-carboxy-pyridinium)methyl-3-cephem-4-carboxylate;

7-[D-α-(4-hydroxy-1,5-naphthyridine-3-carbox-amido)-α-(3,4-dihydroxyphenyl)acetamido]-3-(4′-carboxypyridinium)methyl-3-cephem-4-carboxylate;

7-[D-α-(4-hydroxy-1,5-naphthyridine-3-carbox-amido)-α-(3-chloro-4-hydroxyphenyl)acetamido]-3-(4′-carboxypyridinium)methyl-3-cephem-4-carboxylate;

7[D-α-(4-hydroxy-1,5-naphthyridine-3-carbox-amido)-α-(3-thienyl)acetamido]-3-(4′-carboxypyridinium)-methyl-3-cephem-4-carboxylate;

7-[D-α-(4-hydroxy-1,5-naphthyridine-3-carbox-amido)-α-phenylacetamido]-3-(3′-carboxymethylpyridinium)-methyl-3-cephem-4-carboxylate;

7-[D-α-(4-hydroxy-1,5-naphthyridine-3-carbox-amido)-α-(4-hydroxyphenyl)acetamido]-3-(3′-carboxymethylpyridinium)methyl-3-cephem-4-carboxylate;

7-[D-α-(4-hydroxy-1,5-naphthyridine-3-carbox-amido)-α-(3,4-dihydroxyphenyl)acetamido]-3-(3′-carboxymethylpyridinium)methyl-3-cephem-4-carboxylate;

7-[D-α-(4-hydroxy-1,5-naphthyridine-3-carbox-amido)-α-(3-chloro-4-hydroxyphenyl)acetamido]-3-(3′-carboxymethylpyridinium)methyl-3-cephem-4-carboxylate;

7[D-α-(4-hydroxy-1,5-naphthyridine-3-carbox-amido)-α-(3-thienyl)acetamido]-3-(3′-carboxymethylpyridinium)methyl-3-cephem-4-carboxylate;

7-[D-α-(4-hydroxy-1,5-naphthyridine-3-carbox-amido)-α-phenylacetamido]-3-(4′-carboxymethylpyridinium)-methyl-3-cephem-4-carboxylate;

7-[D-α-(4-hydroxy-1,5-naphthyridine-3-carbox-amido)-α-(4-hydroxyphenyl)acetamido]-3-(4′-carboxymethylpyridinium)methyl-3-cephem-4-carboxylate;

7-[D-α-(4-hydroxy-1,5-naphthyridine-3-carbox-amido)-α-(3,4-dihydroxyphenyl)acetamido]-3-(4′-carboxymethylpyridinium)methyl-3-cephem-4-carboxylate;

7-[D-α-(4-hydroxy-1,5-naphthyridine-3-carbox-amido)-α-(3-chloro-4-hydroxyphenyl)acetamido]-3-(4′-carboxymethylpyridinium)methyl-3-cephem-4-carboxylate;

7-[D-α-(4-hydroxy-1,5-naphthyridine-3-carbox-amido)-α-(3-thienyl)acetamido]-3-(4′-carboxymethylpyridinium)methyl-3-cephem-4-carboxylate;

7-[D-α-(4-hydroxy-1,5-naphthyridine-3-carbox-amido)-α-phenylacetamido]-3-(3′-sulfopyridinium)methyl-3-cephem-4-carboxylate;

7-[D-α-(4-hydroxy-1,5-naphthyridine-3-carbox-amido)-α-(4-hydroxyphenyl)acetamido]-3-(3′-sulfopyridinium)methyl-3-cephem-4-carboxylate;

7-[D-α-(4-hydroxy-1,5-naphthyridine-3-carbox-amido)-α-(3,4-dihydroxyphenyl)acetamido]-3-(3′-sulfopyridinium)methyl-3-cephem-4-carboxylate;

7-[D-α-(4-hydroxy-1,5-naphthyridine-3-carbox-amido)-α-(3-chloro-4-hydroxyphenyl)acetamido]-

3-(3'-sulfopyridinium)methyl-3-cephem-4-carboxylate;

7-[D-α-(4-hydroxy-1,5-naphthyridine-3-carboxamido)-α-(3-thienyl)acetamido]-3-(3'-sulfopyridinium)-methyl-3-cephem-4-carboxylate;

7-[D-α-(4-hydroxy-1,5-naphthyridine-3-carboxamido)-α-phenylacetamido]-3-(3'-carboxypyridinium)-methyl-3-cephem-4-carboxylate;

7-[D-α-(4-hydroxy-1,5-naphthyridine-3-carboxamido)-α-(4-hydroxyphenyl)acetamido]-3-(3'-carboxypyridinium)methyl-3-cephem-4-carboxylate;

7-[D-α-(4-hydroxy-1,5-naphthyridine-3-carboxamido)-α-(3,4-dihydroxyphenyl)acetamido]-3-(3'-carboxypyridinium)methyl-3-cephem-4-carboxylate;

7-[D-α-(4-hydroxy-1,5-naphthyridine-3-carboxamido)-α-(3-chloro-4-hydroxyphenyl)acetamido]-3-(3'-carboxypyridinium)methyl-3-cephem-4-carboxylate;

7-[D-α-(4-hydroxy-1,5-naphthyridine-3-carboxamido)-α-(3-thienyl)acetamido]-3-(3'-carboxypyridinium)-methyl-3-cephem-4-carboxylate;

7-[D-α-(4-hydroxy-1,5-naphthyridine-3-carboxamido)-α-phenylacetamido]-3-(2'-carboxypyridinium)methyl-3-cephem-4carboxylate;

7-[D-α-(4-hydroxy-1,5-naphthyridine-3-carboxamido)-α-(4-hydroxyphenyl)acetamido]-3-(2'-carboxypyridinium)methyl-3-cephem-4-carboxylate;

7-[D-α-(4-hydroxy-1,5-naphthyridine-3-carboxamido)-α-(3,4-dihydroxyphenyl)acetamido]-3-(2'-carboxypyridinium)methyl-3-cephem-4-carboxylate;

7-[D-α-(4-hydroxy-1,5-naphthyridine-3-carboxamido)-α-(3-chloro-4-hydroxyphenyl)acetamido]-3-(2'-carboxypyridinium)methyl-3-cephem-4-carboxylate;

7-[D-α-(4-hydroxy-1,5-naphthyridine-3-carboxamido)-α-(3-thienyl)acetamido]-3-(2'-carboxypyridinium)-methyl-3-cephem-4-carboxylate;

7-[D-α-(4-hydroxy-1,5-naphthyridine-3-carboxamido)-α-phenylacetamido]-3-(4'-sulfoethylpyridinium)-methyl-3-cephem-4-carboxylate;

7[-D-α-(4-hydroxy-1,5-naphthyridine-3-carboxamido)-α-(4-hydroxyphenyl)acetamido]-3-(4'-sulfoethylpyridinium)methyl-3-cephem-4-carboxylate;

7-[D-α-(4-hydroxy-1,5-naphthyridine-3-carboxamido)-α-(3,4-dihydroxyphenyl)acetamido]-3-(4'-sulfoethylpyridinium)methyl-3-cephem-4-carboxylate;

7-[D-α-(4-hydroxy-1,5-naphthyridine-3-carboxamido)-α-(3-chloro-4-hydroxyphenyl)acetamido]-3-(4'-sulfoethylpyridinium)methyl-3-cephem-4-carboxylate;

7-[D-α-(4-hydroxy-1,5-naphthyridine-3-carboxamido)-α-(3-thienyl)acetamido]-3-(4'-sulfoethylpyridinium)-methyl-3-cephem-4-carboxylate;

7-[D-α-(4-hydroxy-1,5-naphthyridine-3-carboxamido)-α-phenylacetamido]-3-[3'-(2-carboxyvinyl)pyridinium]methyl-3-cephem-4-carboxylate;

7-[D-α-(4-hydroxy-1,5-naphthyridine-3-carboxamido)-α-(4-hydroxyphenyl)acetamido]-3-[3'-(2-carboxyvinyl)pyridinium]methyl-3-cephem-4-carboxylate;

7[D-α-(4-hydroxy-1,5-naphthyridine-3-carboxamido)-α-(3,4-dihydroxyphenyl)acetamido]-3-[3'-(2-carboxyvinyl)pyridinium]methyl-3-cephem-4-carboxylate;

7-[D-α-(4-hydroxy-1,5-naphthyridine-3-carboxamido)-α-(3-chloro-4-hydroxyphenyl)acetamido]-3-[3'-(2-carboxyvinyl)pyridinium]methyl-3-cephem-4-carboxylate;

7-[D-α-(4-hydroxy-1,5-naphthyridine-3-carboxamido)-α-(3-thienyl)acetamido]-3-[3'-(2-carboxyvinyl)-pyridinium]-methyl-3-cephem-4-carboxylate;

7-[D-α-(4-hydroxy-1,5-naphthyridine-3-carboxamido)-α-phenylacetamido]-3-(4'-carboxymethylthiopyridinium)methyl-3-cephem-4-carboxylate;

7-[D-α-(4-hydroxy-1,5-naphthyridine-3-carboxamido)-α-(4-hydroxyphenyl)acetamido]-3-(4'-carboxymethylthiopyridinium)methyl-3-cephem-4-carboxylate;

7-[D-α-(4-hydroxy-1,5-naphthyridine-3-carboxamido)-α-(3,4-dihydroxyphenyl)acetamido]-3-(3'-sulfoethylpyridinium)methyl-3-cephem-4-carboxylate;

7-[D-α-(4-hydroxy-1,5-naphthyridine-3-carboxamido)-α-(3-chloro-4-hydroxyphenyl)acetamido]-3-(3'-sulfoethylpyridinium)methyl-3-cephem-4-carboxylate.

There is also provided by the present invention a first process for the preparation of a compound having the formula

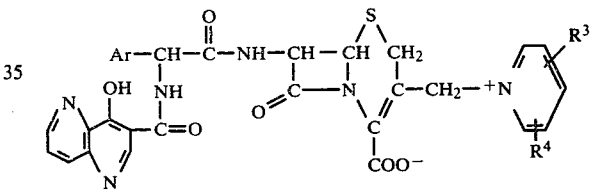

wherein Ar is 

wherein $R^1$ is hydrogen or hydroxy and $R^2$ is hydrogen, hydroxy, methyl, methoxy or chloro and $R^3$ is hydrogen and $R^4$ is carboxyl, carboxymethyl, $-SO_3H$, $-CH_2CH_2COOH$, $-CH=CHCOOH$, $CH_2CH_2SO_3H$ or $-SCH_2COOH$ or $R^3$ and $R^4$ are each carboxyl substituted at the 2,3-, 2,4-, 2,5-, 2,6-, 3,4- or 3,5-positions or an alkali metal salt thereof by reacting with a substituted pyridine having the formula

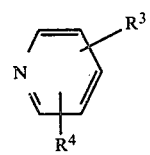

wherein $R^3$ is hydrogen and $R^4$ is carboxyl, carboxymethyl, $-SO_3H_4$, $-CH_2CH_2COOH$, $-CH=CH-COOH$, $-CH_2CH_2SO_3H$ or $-SCH_2COOH$ or $R^3$ and $R^4$ are each carboxyl substituted at the 2,3-, 2,4-, 2,5-, 2,6-, 3,4- or 3,5-positions or an alkali metal salt thereof with a compound having the formula

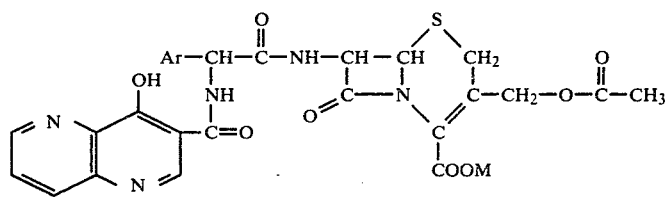

wherein Ar is 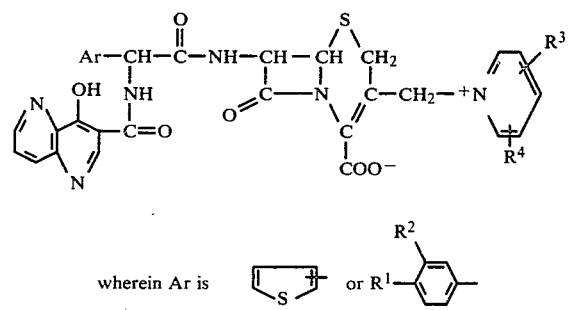

wherein $R^1$ is hydrogen or hydroxy and $R^2$ is hydrogen, hydroxy, methyl, methoxy or chloro and M is hydrogen or a metal and preferably an alkali metal such as sodium or potassium. This reaction is preferably carried out in a solvent and water is preferred. The reaction is carried out at a temperature from room temperature to 100° C.; it is expedited by heating as to about 50° C. Roughly equimolar amounts are used with the preferred procedure being the use of an excess of the substituted pyridine, that is, ten to forty percent. It is also preferred to have KSCN present in the reaction mixture and preferably in an amount by weight which is two to six times (and most preferably four times) the weight of the cephalosporanic acid or its salt.

The compounds of formula II are prepared according to U.S. Pat. No. 4,061,748 and U.K. Pat. No. 1,510,730 by acylation of the corresponding α-amino-arylacetamidocephalosporanic acids which are prepared by well-known methods, e.g. U.S. Pat. Nos. 3,303,193; 3,352,858; 3,489,751; 3,489,752; 3,560,489; 3,634,416; 3,634,418 and Journal of Medicinal Chemistry, 9(5), 746–750 (1966) and 14(2), 117–119 (1971) and J. Antibiotics, 19(6), 243–249 (1966).

There is also provided, according to the present invention, a second process for the preparation of a compound having the formula

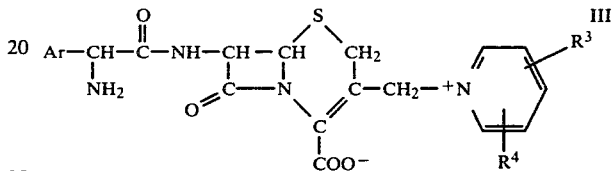

wherein Ar is wherein $R^1$ is hydrogen or hydroxy and $R^2$ is hydrogen, hydroxy, methyl, methoxy or chloro and $R^3$ is hydrogen and $R^4$ is carboxyl, carboxymethyl, —$SO_3H$, —$CH_2CH_2COOH$, —CH=CHCOOH, —$CH_2CH_2SO_3H$, —$SCH_2COOH$ or $R^3$ and $R^4$ are each carboxyl substituted at the 2,3-, 2,4-, 2,5-, 2,6-, 3,4- or 3,5-positions or an alkali metal salt thereof which comprises reacting a compound of the formula

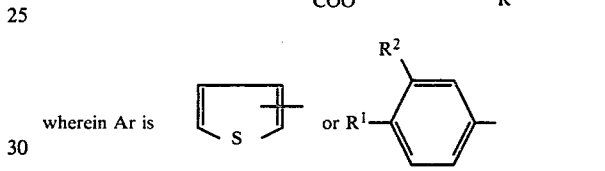

wherein Ar is wherein $R^1$ is hydrogen or hydroxy and $R^2$ is hydrogen, hydroxy, methyl, methoxy or chloro and $R^3$ is hydrogen and $R^4$ is carboxyl, carboxymethyl, —$SO_3H$, —$CH_2CH_2COOH$, —CH=CHCOOH, —$CH_2CH_2SO_3H$, —$SCH_2COOH$ or $R^3$ and $R^4$ are each carboxyl substituted at the 2,3-, 2,4-, 2,5-, 2,6-, 3,4- or 3,5-positions or an alkali metal salt thereof with an acylating derivative of the acid having the formula

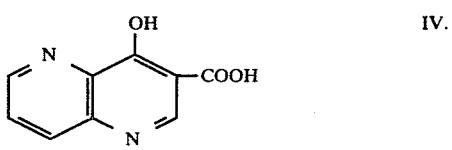

The compounds of the present invention are prepared in the second process by coupling with the compound designated III, with the acid IV or its functional equivalent as an acylating agent for a primary amino group.

Thus, with respect to said acid IV to be used to couple with compound III, functional equivalents include the corresponding acid anhydrides, including mixed anhydrides and particularly the mixed anhydrides prepared from stronger acids such as the lower aliphatic monoesters of carbonic acid, or alkyl and aryl sulfonic acids and of more hindered acids such as diphenylacetic acid. In addition, an acid azide or an active ester or thioester (e.g., with p-nitrophenol, 2,4-dinitrophenol, thiophenol, thioacetic acid) may be used or the free acid itself may be coupled with compound III after first reacting said free acid with N,N'-dimethylchloroforminium chloride [cf. Great Britain 1,008,170 and Novak and Weichet, Experientia XII, 6, 360 (1965)] or by the use of enzymes or of an N,N'-carbonyldiimidazole or an N,N'-carbonylditriazole (cf. South African patent specification No. 63/2684) or a carbodiimide reagent [especially N,N'-dicyclohexylcarbodiimide, N,N'-diisopropylcarbodiimide or N-cyclohexyl-N'-(2-morpholinoethyl)carbodiimide; cf. Sheehan and Hess, J. Amer. Chem. Soc., 77, 1967 (1955)], or of alkynylamine reagent [cf. R. Buijle and H. G. Viehe, Angew. Chem. International Edition 3, 582, (1964)] or of an isoxazolium salt reagent [cf. R. B. Woodward, R. A. Olofson and H. Mayer, J. Amer. Chem. Soc., 83, 1010 (1961)], or of a ketenimine reagent [cf. C. L. Stevens and M. E. Munk, J. Amer. Chem. Soc., 80, 4065 (1958)] or of hexachlorocyclotriphosphatriazine or hexabromocyclotriphosphatriazine (U.S. Pat. No. 3,651,050) or of diphenylphosphoryl azide [DPPA; J. Amer. Chem. Soc., 94, 6203–6205 (1972)] or of diethylphosphoryl cyanide [DEPC; Tetrahedron Letters No. 18, pp. 1595–1598 (1973)] or of diphenyl phosphite [Tetrahedron Letters No. 49, pp. 5047–5050 (1972)]. Another equivalent of the acid chloride is a corresponding azolide, i.e. an amide of the corresponding acid whose amide nitrogen is a member of a quasiaromatic five-membered ring containing at least two nitrogen atoms, i.e. imidazole, pyrazole, the triazoles, benzimidazole, benzotriazole and their substituted derivatives. As an example of the general method for the preparation of an azolide, N,N'-carbonyldiimidazole is reacted with a carboxylic acid in equimolar proportions at room temperature in tetrahydrofuran, chloroform, dimethylformamide or a similar inert solvent to form the carboxylic acid imidazolide in practically quantitative yield with liberation of carbon dioxide and one mole of imidazole. Dicarboxylic acids yield diimidazolide. The by-product, imidazole, precipitates and may be separated and the imidazolide isolated, but this is not essential. The methods for carrying out these reactions to produce a cephalosporin and the methods used to isolate the cephalosporin so produced are well-known in the art.

Mention was made above of the use of enzymes to couple the free acid with compound III. Included in the scope of such processes are the use of an ester, e.g. the methyl ester, of that free acid with enzymes provided by various microorganisms, e.g. those described by T. Takahashi et al., J. Amer. Chem. Soc., 94(11), 4035–4037 (1972) and by T. Nara et al., J. Antibiotics (Japan) 24(5), 321–323 (1971) and in U.S. Pat. No. 3,682,777.

For the coupling of the acid IV as described above with compound III it is also convenient and efficient to utilize as the coupling agent N-ethoxycarbonyl-2-ethoxy-1,2-dihydroquinoline (EEDQ) as described in J. Amer. Chem. Soc., 90, 823–824 and 1652–1653 (1968) and U.S. Pat. No. 3,455,929. The reaction is preferably carried out at 30°–35° C. in benzene, ethanol or tetrahydrofuran using about equimolar quantities of all three reagents followed by conventional isolation.

The compounds of formula III are prepared by reaction of the corresponding α-aminoarylacetamidocephalosporanic acid (in which the α-amino group may be blocked in the usual manner as with a t-butoxycarbonyl group) with one of the substituted pyridines described above under the conditions used in the first process above and then removing the blocking group, if any is present, in the usual manner.

There is also provided by the present invention a third process for the preparation of a compound having the formula

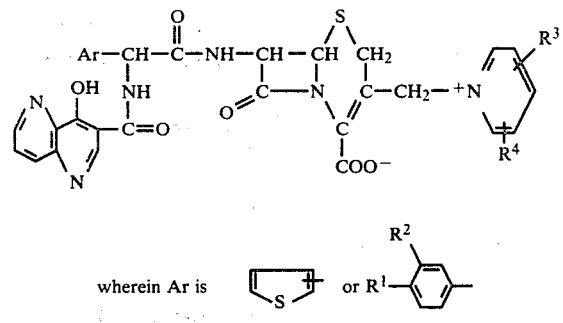

wherein Ar is 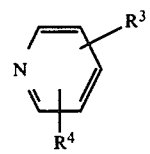

wherein $R^1$ is hydrogen or hydroxy and $R^2$ is hydrogen, hydroxy, methyl, methoxy or chloro and $R^3$ is hydrogen and $R^4$ is carboxyl, carboxymethyl, $-SO_3H$, $-CH_2CH_2COOH$, $-CH=CHCOOH$, $CH_2CH_2SO_3H$ or $-SCH_2COOH$ or $R^3$ and $R^4$ are each carboxyl substituted at the 2,3-, 2,4-, 2,5-, 2,6-, 3,4- or 3,5-positions or an alkali metal salt which comprises two consecutive steps as follows:

FIRST STEP,

The compound having the formula

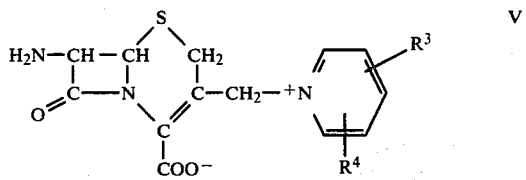

wherein $R^3$ is hydrogen and $R^4$ is carboxyl, carboxymethyl, $-SO_3H$, $-CH_2CH_2COOH$, $-CH=CH-COOH$, $-CH_2CH_2SO_3H$ or $-SCH_2COOH$ or $R^3$ and $R^4$ are each carboxyl substituted at the 2,3-, 2,4-, 2,5-, 2,6-, 3,4- or 3,5-positions is prepared by reacting 7-aminocephalosporanic acid with a substituted pyridine having the formula

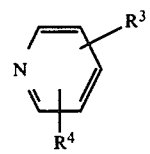

wherein $R^3$ is hydrogen and $R^4$ is carboxyl, carboxymethyl, $-SO_3H$, $-CH_2CH_2COOH$, $-CH=CH-COOH$, $-CH_2CH_2SO_3H$ or $-SCH_2COOH$ or $R^3$ and $R^4$ are each carboxyl substituted at the 2,3-, 2,4-, 2,5-, 2,6-, 3,4- or 3,5-positions. This reaction is preferably carried out in a solvent and water is preferred. The reaction is carried out at a temperature from room temperature to 100° C.; it is expedited by heating as to about 50° C. Roughly equimolar amounts are used with the preferred procedure being the use of an excess of the substituted pyridine, that is, ten to forty percent. It is also preferred to have KSCN present in the reaction mixture and preferably in an amount by weight which is two to six times (and most preferably four times) the weight of the 7-aminocephalosporanic acid or its salt.

SECOND STEP,

A compound of formula V is then reacted with an acylating derivative of an acid having the formula

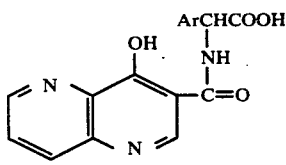

wherein Ar has the meaning set forth above. The conditions are the same as those previously used to couple with acid IV with compound III.

In the treatment of bacterial infections in man, the compounds of this invention are administered parenterally, in accordance with conventional procedures for antibiotic administration, in an amount of from about 5 to 200 mg./kg./day and preferably about 5 to 20 mg./kg./day in divided dosage, e.g. three to four times a day. They are administered in dosage units containing, for example, 125, 250 or 500 mg. of active ingredient with suitable physiologically acceptable carriers or excipients. The dosage units are preferably in the form of liquid preparations such as solutions or suspensions.

Also included within the present invention are pharmaceutical compositions comprising a mixture of an antibacterially effective amount of a compound of the present invention and a semisynthetic penicillin or another cephalosporin or a cephamycin or a β-lactamase inhibitor or an aminoglycoside antibiotic.

There is further provided by the present invention a pharmaceutical composition comprising an antibacterial effective amount of a compound having the formula

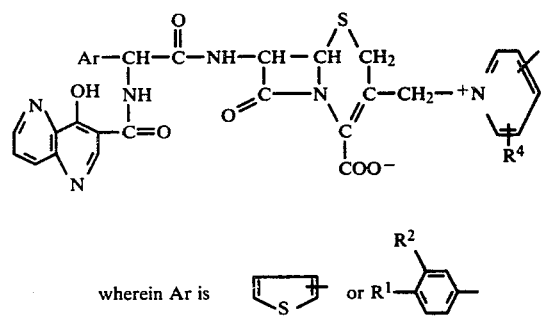

wherein $R^1$ is hydrogen or hydroxy and $R^2$ is hydrogen, hydroxy, methyl, methoxy or chloro and $R^3$ is hydrogen and $R^4$ is carboxyl, carboxymethyl, —SO$_3$H, —CH$_2$CH$_2$COOH, —CH=CHCOOH, —CH$_2$CH$_2$SO$_3$H, —SCH$_2$COOH or $R^3$ and $R^4$ are each carboxyl substituted at the 2,3-, 2,4-, 2,5-, 2,6-, 3,4- or 3,5-positions or an alkali metal salt thereof.

There is further provided by the present invention a method of treating bacterial infections comprising administering by injection to an infected warm-blooded animal, including man, an effective but nontoxic dose of a compound having the formula

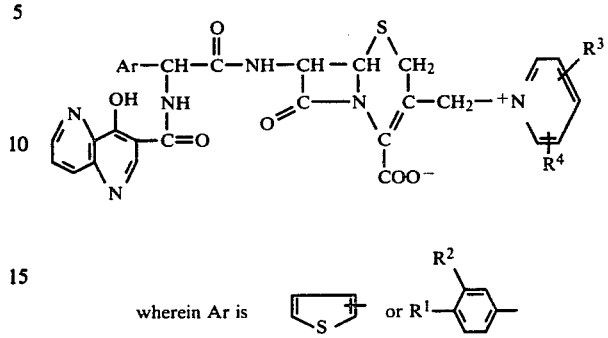

wherein $R^1$ is hydrogen or hydroxy and $R^2$ is hydrogen, hydroxy, methyl, methoxy or chloro and $R^3$ is hydrogen and $R^4$ is carboxyl, carboxymethyl, —SO$_3$H, —CH$_2$CH$_2$COOH, —CH=CHCOOH, —CH$_2$CH$_2$SO$_3$H, —SCH$_2$COOH or $R^3$ and $R^4$ are each carboxyl substituted at the 2,3-, 2,4-, 2,5-, 2,6-, 3,4- or 3,5-positions or an alkali metal salt thereof.

There is also provided by the present invention a method for combatting *Pseudomonas aeruginosa* infections which comprises administering to a warm-blooded mammal infected with a *Pseudomonas aeruginosa* infection an amount effective for treating said *Pseudomonas aeruginosa* infection of a composition comprising a compound having the formula

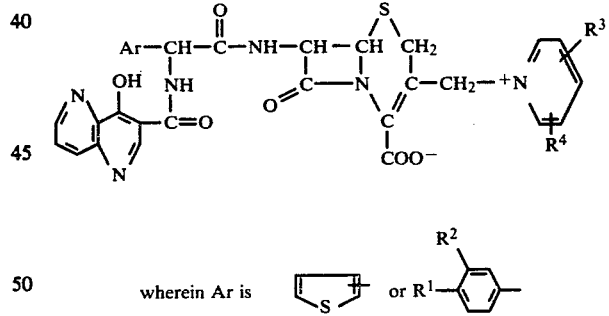

wherein $R^1$ is hydrogen or hydroxy and $R^2$ is hydrogen, hydroxy, methyl, methoxy or chloro and $R^3$ is hydrogen and $R^4$ is carboxyl, carboxymethyl, —SO$_3$H, —CH$_2$CH$_2$COOH, —CH=CHCOOH, —CH$_2$CH$_2$SO$_3$H, —SCH$_2$COOH or $R^3$ and $R^4$ are each carboxyl substituted at the 2,3-, 2,4-, 2,5-, 2,6-, 3,4- or 3,5-positions or an alkali metal salt thereof.

HP-20 is a macroreticular adsorbent resin in the form of insoluble beads of porous polymer. They are macroporous, nonionic, cross-linked polystyrene polymers.

The following examples are for purposes of illustration only.

DESCRIPTION OF THE PREFERRED EMBODIMENTS

EXAMPLE 1

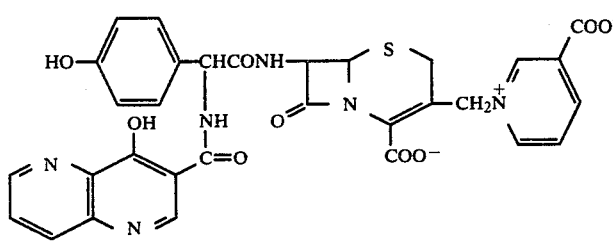

BB-S579

7-[D-α-(4-Hydroxy-1,5-naphthyridine-3-carboxamido-α-(4-hydroxyphenyl)acetamido]-3-(3-carboxypyridinium)methyl-3-cephem-4-carboxylate, (BB-S579)

A mixture of sodium 7-[D-α-(4-hydroxy-1,5-naphthyridine-3-carboxamido)-α-(4-hydroxyphenyl)acetamido]cephalosporanate[1]) (BB-S550), (555 mg., 0.9 m.mole), nicotinic acid (330 mg., 2.7 m.moles) and KSCN (2.2 g., 23 m.moles) in 2 ml. of water was stirred overnight at 50°–52° C. The reaction mixture was diluted with 10 ml. of water and chromatographed on a column of HP-20 (90 ml.; high porous polymer resin, Nippon Rensui Co.), eluting with 800 ml. of water, 600 ml. of 30% aqueous MeOH (methanol) and 500 ml. of 50% aqueous MeOH successively. The eluate was collected in 20-ml. fractions and monitored by tlc (silica gel plate, $CH_3CN/H_2O=4/1$, detected with $I_2$). The desired product was found in fraction numbers 44 through 54 eluted with 30% aqueous MeOH which were combined and concentrated under diminished pressure. To the concentrates was added 50 ml. of acetone and the resulting precipitate was collected by filtration and washed with acetone to afford 124 mg. of the product BB-S579. M.p. >300° C.

[1] Japan Kokai 51-32576 (3/19/76, Sumitomo); U.S. Pat. No. 4,061,748; U.K. 1,510,730.

A suspension of the free acid (105 mg., 0.16 m.mole) in 1 ml. of water was adjusted to pH 7.5 by adding 0.1 M $Na_2CO_3$ (0.8 ml. was required) under stirring at room temperature. During the addition the suspension turned to a solution. A small amount of insolubles was removed by filtration and the filtrate lyophilized to afford 72 mg. (14% yield from sodium 7-[D-α-(4-hydroxy-1,5-naphthyridine-3-carboxamido)-α-(4-hydroxyphenyl)acetamido]cephalosporanate) of the sodium salt of 7-[D-α-(4-hydroxy-1,5-naphthyridine-3-carboxamido)-α-(4-hydroxyphenyl)acetamido]-3-(3-carboxypyridinium)methyl-3-cephem-4-carboxylate (BB-S579). M.p. >300° C.

ir: $\nu_{max}^{KBr}$ 3400, 1765, 1640, 1610, 1520 $cm^{-1}$. uv: $\lambda_{max}^{Buffer\ (pH\ 7)}$ 256 nm ($\epsilon$, 35700), 310 nm ($\epsilon$, 8400).

EXAMPLE 2

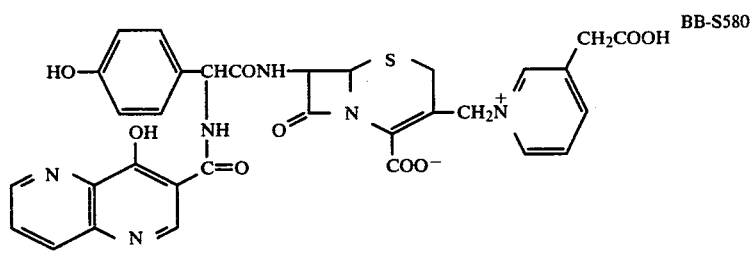

BB-S580

7-[D-α-(4-Hydroxy-1,5-naphthyridine-3-carboxamido)-α-(4-hydroxyphenyl)acetamido]-3-(3-carboxymethylpyridinium)methyl-3-cephem-4-carboxylate, (BB-S580)

BB-S580 was prepared from sodium 7-[D-α-(4-hydroxy-1,5-naphthyridine-3-carboxamido)-α-(4-hydroxyphenyl)acetamido]-cephalosporanate (555 mg., 0.9 m.mole), 3-pyridylacetic acid (370 mg., 2.7 m.moles) and KSCN (2.2 g., 23 m.moles) and converted to the sodium salt by a procedure similar to Example 1 for BB-S579. Yield 15%, m.p. >300° C.

ir: $\nu_{max}^{KBr}$ 3400, 1765, 1640, 1610, 1520 $cm^{-1}$. uv: $\lambda_{max}^{Buffer\ (pH\ 7)}$ 255 nm ($\epsilon$, 35200), 310 nm ($\epsilon$, 8500).

EXAMPLE 3

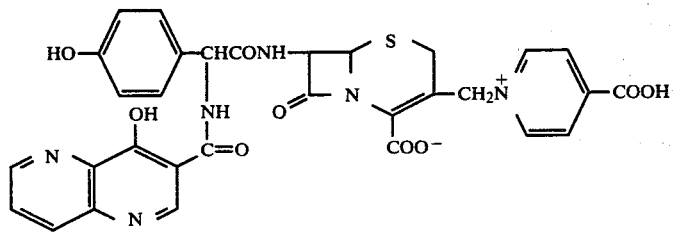

BB-S584

7-[D-α-(4-Hydroxy-1,5-naphthyridine-3-carboxamido)-α-(4-hydroxyphenyl)acetamido]-3-(4-carboxypyridinium)methyl-3-cephem-4-carboxylate, (BB-S584)

A mixture of sodium 7-[D-α-(4-hydroxy-1,5-naphthyridine-3-carboxamido)-α-(4-hydroxyphenyl- )acetamido]cephalosporanate (500 mg., 0.81 m.mole), isonicotinic acid (400 mg., 3.2 m.moles) and KSCN (2 g., 20 m.moles) was kept standing overnight at 50°–52° C. The reaction mixture was subjected to HP-20 column chromatography eluting with 800 ml. of water and 500 ml. of 30% MeOH. The desired product was found in fractions eluted with 30% aqueous MeOH, which was worked up by the procedure described in Example 1 for BB-S579 to afford BB-S584 sodium salt in 16% yield. M.p. >260° C. (dec.).

ir: $\nu_{max}^{KBr}$ 3400, 1765, 1640, 1610, 1520 cm$^{-1}$. uv: $\lambda_{max}^{pH\ 7\ Buffer}$ 255 nm ($\epsilon$, 44000), 310 nm ($\epsilon$, 12700).

EXAMPLE 4

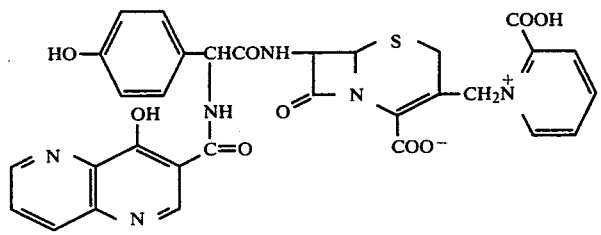

7-[D-α-(4-Hydroxy-1,5-naphthyridine-3-carboxamido)-α-(4-hydroxyphenyl)acetamido]-3-(2-carboxypyridinium)methyl-3-cephem-4-carboxylate, (BB-S585)

According to a procedure similar to Example 1 for BB-S579, BB-S585 was prepared from sodium 7-[D-α-(4-hydroxy-1,5-naphthyridine-3-carboxamido)-α-(4-hydroxyphenyl)acetamido]-cephalosporanate (555 mg., 0.9 m.mole), picolinic acid (443 mg., 3.6 m.moles) and KSCN (2.2 g., 23 m.moles) and converted to the sodium salt which began to melt around 170° C. with gradual decomposition. Yield 13%.

ir: $\nu_{max}^{KBr}$ 3400, 1765, 1650, 1610, 1550, 1520 cm$^{-1}$. uv: $\lambda_{max}^{pH\ 7\ Buffer}$ 254 nm ($\epsilon$, 46300), 311 nm ($\epsilon$, 13600).

EXAMPLE 5

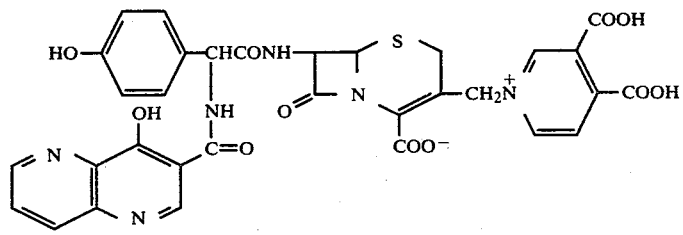

BB-S586

7-[D-α-(4-Hydroxy-1,5-naphthyridine-3-carboxamido)-α-(4-hydroxyphenyl)acetamido]-3-(3,4-dicarboxypyridinium)methyl-3-cephem-4-carboxylate, (BB-S586)

According to a procedure similar to Example 1 for BB-S579, BB-S586 was prepared from sodium 7-[D-α-(4-hydroxy-1,5-naphthyridine-3-carboxamido)-α-(4-hydroxyphenyl)acetamido]-cephalosporanate (555 mg., 0.9 m.mole), pyridine-3,4-dicarboxylic acid (601 mg., 3.6 m.moles), NaHCO$_3$ (301 mg., 3.6 m.moles) and KSCN (2.2 g., 23 m.moles) and converted to the sodium salt, which began to melt around 210° C. with gradual decomposition. Yield 3%.

BB-S585 ir: $\nu_{max}^{KBr}$ 3400, 1765, 1640, 1610, 1540, 1520 cm$^{-1}$. uv: $\lambda_{max}^{pH\ 7\ Buffer}$ 256 nm ($\epsilon$, 32000), 310 nm ($\epsilon$, 7800).

EXAMPLE 6

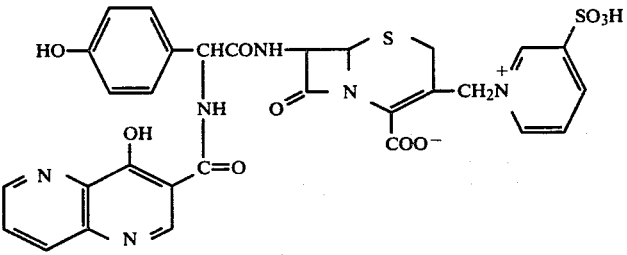

BB-S587

7-[D-α-(4-Hydroxy-1,5-naphthyridine-3-carboxamido)-α-(4-hydroxyphenyl)acetamido]-3-(3-sulfopyridinium)-methyl-3-cephem-4-carboxylate, (BB-S587).

According to a procedure similar to Example 1 for BB-S579, BB-S587 was prepared from sodium 7-[D-α-(4-hydroxy-1,5-naphthyridine-3-carboxamido)-α-(4-hydroxyphenyl)acetamido]cephalosporanate (500 mg., 0.81 m.mole), sodium pyridine-3-sulfonate dihydrate (694 mg., 3.2 m.moles) and KSCN (2 g., 20 m.moles) and converted to the sodium salt which began to melt around 230° C. with gradual decomposition. Yield 6%.

ir: $\nu_{max}^{KBr}$ 3400, 3250, 1770, 1650, 1610, 1520, 1050 cm$^{-1}$. uv: $\lambda_{max}^{pH\ 7\ Buffer}$ 256 nm ($\epsilon$, 40200), 310 nm ($\epsilon$, 9500).

EXAMPLE 7

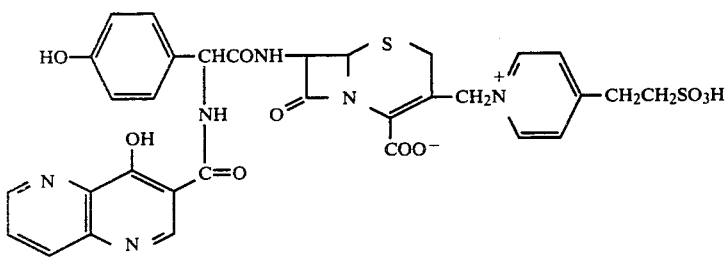

BB-S588

7-[D-α-(4-Hydroxy-1,5-naphthyridine-3-carboxamido)-α-(4-hydroxyphenyl)acetamido]-3-(4-sulfoethyl-pyridinium)methyl-3-cephem-4-carboxylate, (BB-S588).

According to a procedure similar to Example 1 for BB-S579, BB-S588 was prepared from sodium 7-[D-α-(4-hydroxy-1,5-naphthyridine-3-carboxamido)-α-(4-hydroxyphenyl)acetamido]cephalosporanate (500 mg., 0.81 m.mole), 2-(4-pyridyl)ethanesulfonic acid (600 mg., 3.2 m.moles), Na$_2$CO$_3$ (159 mg., 1.5 m.moles) and KSCN (2 g., 20 m.moles) and converted to the sodium salt which began to melt around 165° C. with gradual decomposition. Yield 12%.

ir: $\nu_{max}^{KBr}$ 3450, 3250, 1770, 1640, 1610, 1520, 1045 cm$^{-1}$. uv: $\lambda_{max}^{pH\ 7\ Buffer}$ 256 nm ($\epsilon$, 38000), 310 nm ($\epsilon$, 8200).

EXAMPLE 8

7-[D-α-(4-Hydroxy-1,5-naphthyridine-3-carboxamido)-α-(4-hydroxyphenyl)acetamido]-3-[3-(2-carboxyvinyl)-pyridinium]methyl-3-cephem-4-carboxylate, (BB-S589).

According to a procedure similar to Example 1 for BB-S579, BB-S589 was prepared from sodium 7-[D-α-(4-hydroxy-1,5-naphthyridine-3-carboxamido)-α-(4-hydroxyphenyl)acetamido]cephalosporanate (500 mg., 0.81 m.mole), β-(3-pyridyl)acrylic acid (484 mg., 3.2 m.moles) and KSCN (2 g., 20 m.moles) and converted to the sodium salt, which began to melt around 210° C. with gradual decomposition. Yield 9%.

ir: $\nu_{max}^{KBr}$ 3400, 3250, 1765, 1650, 1610, 1520 cm$^{-1}$. uv: $\lambda_{max}^{pH\ 7\ Buffer}$ 256 nm ($\epsilon$, 41000), 310 nm ($\epsilon$, 9700).

EXAMPLE 9

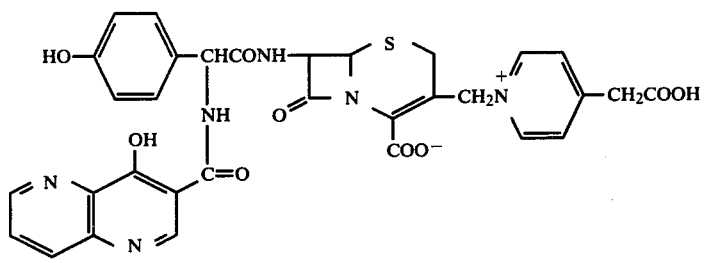

BB-S591

7-[D-α-(4-Hydroxy-1,5-naphthyridine-3-carboxamido)-α-(4-hydroxyphenyl)acetamido]-3-(4-carboxymethyl-pyridinium)methyl-3-cephem-4-carboxylate, (BB-S591)

According to a procedure similar to Example 1 for BB-S579, BB-S591 was prepared from sodium 7-[D-α-(4-hydroxy-1,5-naphthyridine-3-carboxamido)-α-(4-hydroxyphenyl)acetamido]-cephalosporanate (500 mg., 0.81 m.mole), 4-pyridylacetic acid hydrochloride (722 mg., 2.4 m.moles), NaHCO$_3$ (168 mg., 2 m.moles) and KSCN 2 g., 20 m.moles) and converted to the sodium

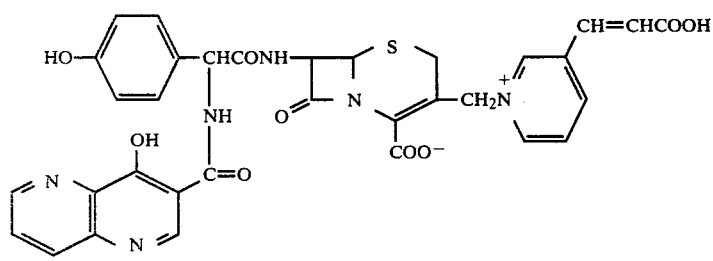

BB-S589 salt which began to melt around 160° C. with gradual decomposition. Yield 39%.

ir: $\nu_{max}^{KBr}$ 3400, 3250, 1775, 1640, 1610, 1520 cm$^{-1}$.
uv: $\lambda_{max}^{pH\ 7\ buffer}$ 256 nm ($\epsilon$, 25000), 310 nm ($\epsilon$, 5800).

EXAMPLE 10

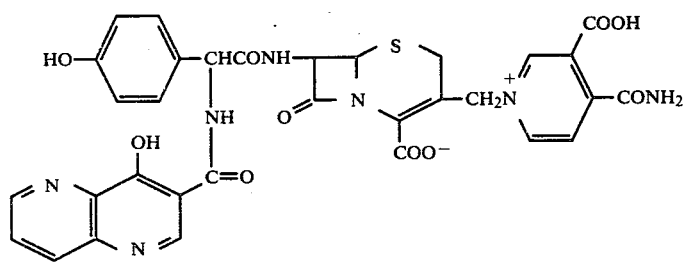

BB-S592

7-[D-α-(4-Hydroxy-1,5-naphthyridine-3-carboxamido)-α-(4-hydroxyphenyl)acetamido]-3-(4-carbamoyl-3-carboxypyridinium)methyl-3-cephem-4-carboxylate, (BB-S592)

According to a procedure similar to Example 1 for BB-S579, BB-S592 was prepared from sodium 7-[D-α-(4-hydroxy-1,5-naphthyridine-3-carboxamido)-α-(4-hydroxyphenyl)acetamido]-cephalosporanate (500 mg., 0.81 m.mole), 4-carbamoylnicotinic acid ammonium salt monohydrate (439 mg., 2.5 m.moles), NaHCO$_3$ (168 mg., 2 m.moles) and KSCN (2 g., 20 m.moles) and converted to the sodium salt which began to melt around 220° C. with gradual decomposition. Yield 37%.

ir: $\nu_{max}^{KBr}$ 3400, 3250, 1760, 1650, 1610, 1520 cm$^{-1}$.
uv: $\lambda_{max}^{pH\ 7\ buffer}$ 256 nm ($\epsilon$, 38000), 310 nm ($\epsilon$, 11000).

EXAMPLE 11

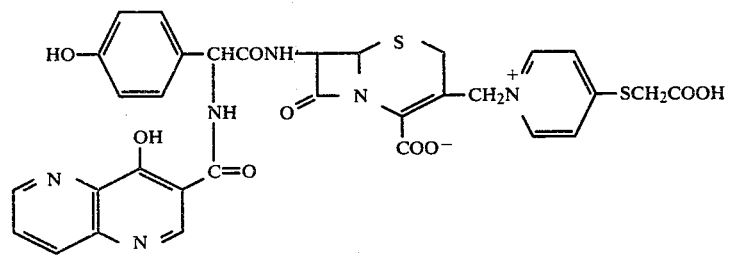

BB-S599

7-[D-α-(4-Hydroxy-1,5-naphthyridine-3-carboxamido)-α-(4-hydroxyphenyl)acetamido]-3-(4-carboxymethylthiopyridinium)-methyl-3-cephem-4-carboxylate, (BB-S599)

According to a procedure similar to Example 1 for BB-S579, BB-S599 was prepared from sodium 7-[D-α-(4-hydroxy-1,5-naphthyridine-3-carboxamido)-α-(4-hydroxyphenyl)acetamido]cephalosporanate (617 mg., 1 m.mole), 4-pyridylthio)acetic acid (670 mg., 4 m.moles) and KSCN (2.4 g., 25 m.moles) and converted to the sodium salt which began to melt aroung 220° C. with gradual decomposition. Yield 193 mg. (27%).

ir: $\nu_{max}^{KBr}$ 3400, 1765, 1650, 1610, 1515 cm$^{-1}$. uv: $\lambda_{max}^{pH\ 7\ buffer}$ 255 nm ($\epsilon$, 32300), 310 nm ($\epsilon$, 19800).

EXAMPLE 12

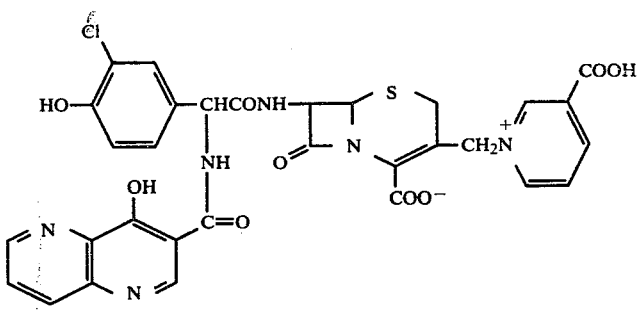

BB-S600

7-[D-α-(4-Hydroxy-1,5-naphthyridine-3-carboxamido)-α-(3-chloro-4-hydroxyphenyl)acetamido]-3-(3-carboxypyridinium)-methyl-3-cephem-4-carboxylate, (BB-S600)

To a solution of nicotinic acid (454 mg., 3.7 m.moles) and NaHCO$_3$ (310 mg., 3.7 m.moles) in 2 ml. of water were added sodium 7-[D-α-(4-hydroxy-1,5-naphthyridine-3-carboxamido)-α-(3-chloro-4-hydroxyphenyl)acetamido]cephalosporanate[2], (600 mg., 0.92 m.mole) and KSCN (2.2 g., 23 m.moles) and the mixture was kept standing overnight at 50–52° C. The reaction mixture was chromatographed on an HP-20 column eluting with 30% aqueous MeOH as an eluent. The fractions which contained the desired product were combined and evaporated to give 160 mg. (24%) of the title compound which started to melt around 300° C. with gradual decomposition.

[2] Japan Kokai 51-32576 (3/19/76, Sumitomo); U.S. Pat. No. 4,061,748; U.K. Pat. No. 1,510,730.

ir: $\nu_{max}^{KBr}$ 3400, 3200, 1765, 1640, 1610, 1520 cm$^{-1}$.
uv: $\lambda_{max}^{pH\ 7\ buffer}$ 255 nm ($\epsilon$, 35200), 310 nm ($\epsilon$, 9500).

EXAMPLE 13

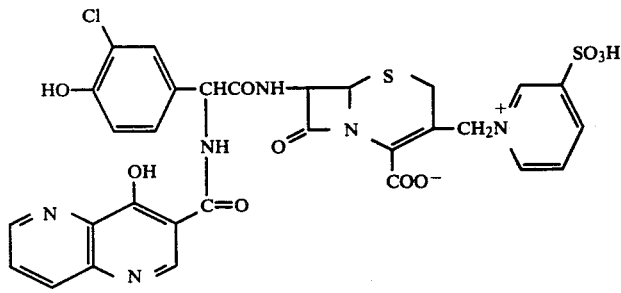

BB-S601

7-[D-α-(4-Hydroxy-1,5-naphthyridine-3-carboxamido)-α-(3-chloro-4-hydroxyphenyl)acetamido]-3-(3-sulfopyridinium)methyl-3-cephem-4-carboxylate, (BB-S601)

According to a procedure similar to Example 12 for BB-S600, sodium 7-[D-α-(4-hydroxy-1,5-naphthyridine-3-carboxamido)-α-(3-chloro-4-hydroxyphenyl)acetamido]cephalosporanate (600 mg., 0.92 m.mole) was treated with sodium pyridine-3-sulfonate dihydrate (881 mg., 3.7 m.moles) in the presence of KSCN (2.2 g., 23 m.moles) in water to afford BB-S601. Yield 30 mg. (4.4%). M.p. >270° C. (decomp.).

ir: $\nu_{max}^{KBr}$ 3400, 3250, 1765, 1640, 1610, 1570, 1520, 1045 cm$^{-1}$. uv: $\lambda_{max}^{pH\ 7\ buffer}$ 225 nm ($\epsilon$, 38000), 310 nm ($\epsilon$, 9500).

EXAMPLE 14

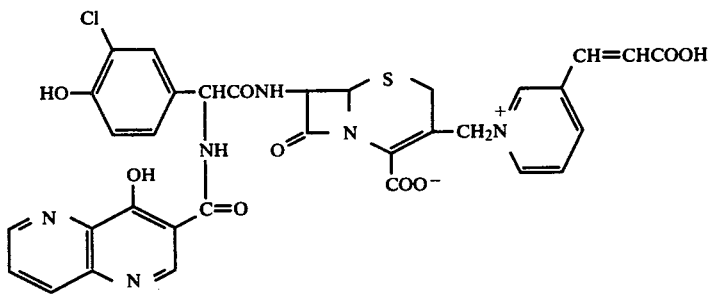

BB-S602

7-[D-α-(4-Hydroxy-1,5-naphthyridine-3-carboxamido)-α-(3-chloro-4-hydroxyphenyl)acetamido]-3-(3-carboxyvinylpyridinium)-methyl-3-cephem-4-carboxylate, (BB-S602)

According to a procedure similar to Example 12 for BB-S600, sodium 7-[D-α-(4-hydroxy-1,5-naphthyridine-3-carboxamido)-α-(3-chloro-4-hydroxyphenyl)acetamido]cephalosporanate (600 mg., 0.92 m.mole) was treated with 3-pyridylacrylic acid (551 mg., 3.7 m.moles) in the presence of KSCN (2.2 g., 23 m.moles) in water to afford BB-S602. Yield 190 mg. (26%). M.p. >230° C. (decomp.)

ir: $\nu_{max}^{KBr}$ 3400, 3200, 1765, 1640, 1610, 1570, 1520 cm$^{-1}$. uv: $\lambda_{max}^{pH\ 7}$ buffer 225 nm ($\epsilon$m 41300), 310 nm ($\epsilon$, 10900).

EXAMPLE 15

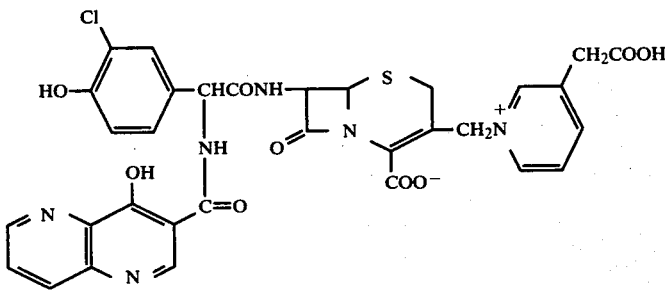

BB-S604

7-[D-α-(4-Hydroxy-1,5-naphthyridine-3-carboxamido)-α-(3-chloro-4-hydroxyphenyl)acetamido]-3-(3-carboxymethylpyridinium)-methyl-3-cephem-4-carboxylate, (BB-S604)

According to a procedure similar to Example 12 for BB-S600, sodium 7-[D-α-(4-hydroxy-1,5-naphthyridine-3-carboxamido)aα-(3-chloro-4-hydroxyphenyl)acetamido]cephalosporanate (600 mg., 0.92 m.mole) was treated with 3-pyridylacetic acid (507 mg., 3.7 m.moles) in the presence of KSCN (2.2 g., 23 m.moles) in water to afford BB-S604. Yield 119 mg. (18%). M.p. >300° C.

ir: $\nu_{max}^{KBr}$ 3400, 3250, 1765, 1650, 1610, 1530 cm$^{-1}$.
uv: $\lambda_{max}^{pH\ 7\ buffer}$ 255 nm (ε, 33990), 310 nm (ε, 9500).

EXAMPLE 16

7-[D-α-(4-Hydroxy-1,5-naphthyridine-3-carboxamido)-α-(3-chloro-4-hydroxyphenyl)acetamido]-3-(4-sulfoethylpyridinium)-methyl-3-cephem-4-carboxylate, (BB-S605)

According to a procedure similar to Example 12 for BB-S600, sodium 7-[D-α-(4-hydroxy-1,5-naphthyridine-3-carboxamido)-α-(3-chloro-4-hydroxyphenyl)acetamido]cephalosporanate (600 mg., 0.92 m.mole) was treated with 4-pyridylethylsulfonic acid (692 mg., 3.7 m.moles) in the presence of KSCN (2.2 g., 23 m.moles) in water to afford BB-S605. Yield, 139 mg. (19%). m.P. >270° C. (decomp.)

ir: $\nu_{max}^{KBr}$ 3400, 3250, 1770, 1650, 1610, 1530, 1050 cm$^{-1}$. uv: $\lambda_{max}^{pH\ 7\ buffer}$ 255 nm (ε, 33700), 310 nm (ε, 9000).

EXAMPLE 17

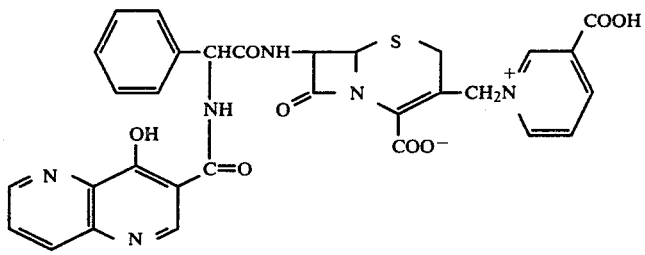

BB-S606

7-[D-α-(4-Hydroxy-1,5-naphthyridine-3-carboxamido)-α-phenyl-acetamido]-3-(3-carboxypyridinium)methyl-3-cephem-4-carboxylate, (BB-S606)

To a mixture of nicotinic acid (492 mg., 4 m.moles) and NaHCO$_3$ (336 mg., 4 m.moles) in 2 ml. of water were added sodium 7-[D-α-(4-hydroxy-1,5-naphthyridine-3-carboxamido)-α-phenylacetamido]cephalosporanate[3], (600 mg., 1 m.mole) and KSCN (2.4 g., 25 m.moles) and the mixture was allowed to stand overnight at 50°–52° C. The reaction mixture was placed on the top of an HP-20 column (φ 10 mm., 90 ml.). The column was developed with 1 L each of water, 30% aqueous MeOH and 50% aqueous MeOH. The eluate was collected in 20-ml. fractions, monitoring with tlc (silica-gel plate, CH$_3$CN:H$_2$O=4:1, detected with I$_2$). The desired product was found in the fractions eluted with 30% aqueous MeOH, which were combined and concentrated under reduced pressure. The concentrates showing a neutral pH were lyophilized to give 105 mg. (16%) of BB-S606, which dissolved readily in water to give a 25% (w/v) solution. It started to melt around 280° C. with gradual decomposition.

[3]Japan Kokai 51-32576 (3/19/76, Sumitomo); U.S. Pat. No. 4,061,748; U.K. Pat. No. 1,510,730.

ir: $\nu_{max}^{KBr}$ 3400, 3250, 1770, 1650, 1610, 1530 cm$^{-1}$.
uv: $\lambda_{max}^{pH\ 7\ buffer}$ 255 nm (ε, 24000), 310 nm (εm 7300).

EXAMPLE 18

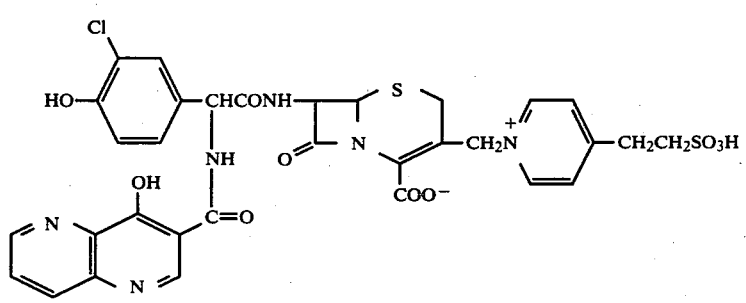

BB-S605

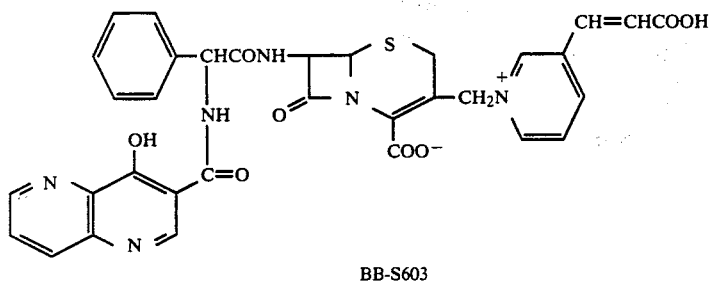

BB-S603

7-[D-α-(4-Hydroxy-1,5-naphthyridine-3-carboxamide)-α-phenyl-acetamido]-3-(3-carboxyvinylpyridinium)-methyl-3-cephem-4-carboxylate, (BB-S603)

According to a procedure similar to Example 17 for BB-S606, sodium 7-[D-α-(4-hydroxy-1,5-naphthyridine-3-carboxamido)-α-phenylacetamido]cephalosporanate (600 mg., 1 m.mole) was treated with β-(3-pyridyl)acrylic acid (600 mg., 4 m.moles) in the presence of KSCN (2.4 g., 25 m.moles) in water to afford BB-S603. Yield 175 mg. (25%). M.p. >295° C. (dec.)

ir: $\nu_{max}^{KBr}$ 3400, 3250, 1765, 1650, 1610, 1570, 1530 cm$^{-1}$. uv: $\lambda_{max}^{pH\ 7\ buffer}$ 255 nm (ε, 33000), 310 nm (ε, 9000).

EXAMPLE 19

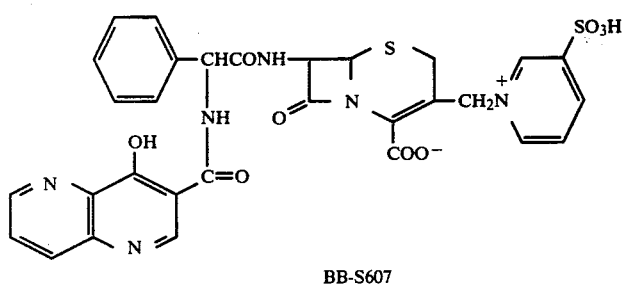

BB-S607

7-[D-α-(4-Hydroxy-1,5-naphthyridine-3-carboxamido)-α-phenylacetamido]-3-(3-sulfopyridinium)methyl-3-cephem-4-carboxylate, (BB-S607)

According to a procedure similar to Example 17 for BB-S606, sodium 7-[D-α-(4-hydroxy-1,5-naphthyridine-3-carboxamido)-α-phenylacetamido]cephalosporanate (600 mg., 1 m.mole) was treated with sodium pyridine-3-sulfonate dihydrate (870 mg., 4 m.moles) in the presence of KSCN (2.4 g., 25 m.moles) in water to afford BB-S607. Yield 40 mg. (6%). M.p. >260° C. (dec.).

ir: $\nu_{max}^{KBr}$ 3400, 3250, 1775, 1660, 1620, 1540, 1050 cm$^{-1}$. uv: $\lambda_{max}^{pH\ 7\ buffer}$ 256 nm (ε, 28000), 310 nm (ε, 7600).

EXAMPLE 20

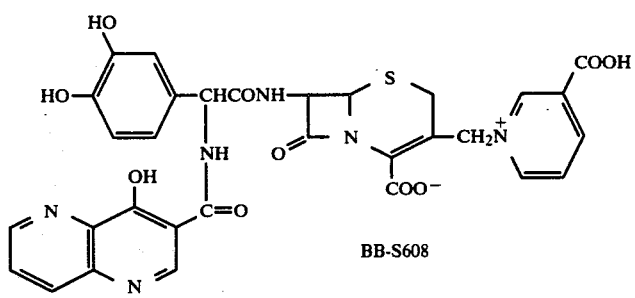

BB-S608

7-]D-α-(4-Hydroxy-1,5-naphthyridine-3-carboxamido)-α-(3,4-dihydroxyphenyl)acetamido]-3-(3-carboxypyridinium)methyl-3-cephem-4-carboxylate, (BB-S608)

To a solution of nicotinic acid (492 mg., 4 m.moles) in 2 ml. of water containing NaHCO$_3$ (336 mg., 4 m.moles) were added KSCN (2.4 g., 25 m.moles) and sodium 7-[D-α-(4-hydroxy-1,5-naphthyridine-3-carboxamido)-α-(3,4-dihydroxyphenyl)-acetamido]cephalosporanate[4] (633 mg., 1 m.mole). The mixture was kept standing overnight at 50–52° C. The reaction mixture was chromatographed on an HP-20 (90 ml.) column by eluting with 1 L of water and 1 L of 30% aqueous MeOH successively. The eluate was collected in 20-ml. fractions, monitoring with tlc (silica-gel, CH$_3$CN:H$_2$O=4:1, detected with I$_2$). The fractions 57–69 were combined, concentrated under reduced pressure and finally lyophilized to give 110 mg. (16%) of BB-S608 which melted at >290° C. with gradual decomposition.

[4] Japan Kokai 51-32576 (3/19/76, Sumitomo); U.S. Pat. No. 4,061,748; U.K. Pat. No. 1,510,730.

ir: $\nu_{max}^{KBr}$ 3400, 3250, 1770, 1640, 1610, 1530 cm$^{-1}$.
uv: $\lambda_{max}^{pH\ 7\ buffer}$ 255 nm ($\epsilon$, 34000), 310 nm ($\epsilon$, 9000).

EXAMPLE 21

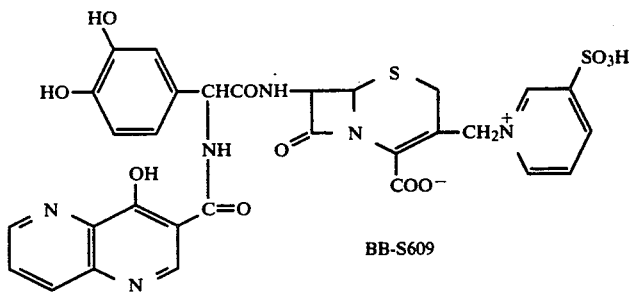

BB-S609

7-[D-α-(4-Hydroxy-1,5-naphthyridine-3-carboxamido)-α-(3,4-dihydroxyphenyl)acetamido]-3-(3-sulfopyridinium)methyl-3-cephem-4-carboxylate, (BB-S609)

According to a procedure similar to Example 20 for BB-S608, sodium 7-[D-α-(4-hydroxy-1,5-naphthyridine-3-carboxamido)-α-(3,4-dihydroxyphenyl)acetamido]cephalosporanate (633 mg., 1 m.mole) was treated with sodium pyridine-3sulfonate (870 mg., 4 m.moles) in the presence of KSCN (2.4 g., 25 m.moles) in water to afford BB-S609. Yield 136 mg. (19%). M.p. >280° C. (decomp.). ir: $\nu_{max}^{KBr}$ 3400, 3250, 1770, 1650, 1610, 1530, 1050 cm$^{-1}$. uv: $\lambda_{max}^{pH\ 7\ buffer}$ 255 nm ($\epsilon$, 34600), 310 nm ($\epsilon$, 9000).

EXAMPLE 22

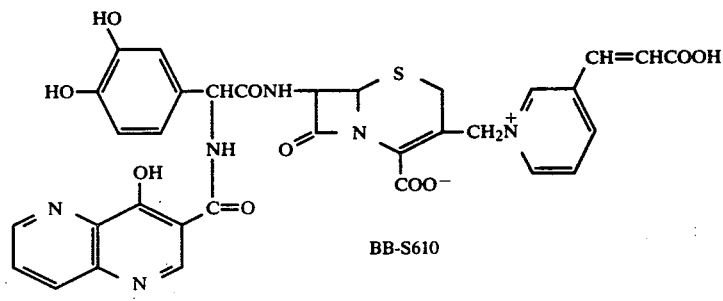

BB-S610

7-[D-α-(4-Hydroxy-1,5-naphthyridine-3-carboxamido-α-(3,4-dihydroxyphenyl)acetamido]-3-(3-carboxyvinylpyridinium)methyl-3-cephem-4-carboxylate, (BB-S610)

According to a procedure similar to Example 20 for BB-S608, sodium 7-[D-α-(4-hydroxy-1,5-naphthyridine-3-carboxamido)-α-(3,4-dihydroxyphenyl)acetamido]cephalosporanate (633.5 mg., 1 m.mole ) was treated with 3-pyridylacrylic acid (600 mg., 4 m.moles) in the presence of KSCN (2.4 g., 25 m.moles) in water to afford BB-S610. Yield 176 mg. (24%). M.p. >300° C. (decomp.).

ir: $\nu_{max}^{KBr}$ 3400, 3250, 1760, 1650, 1610, 1530 cm$^{-1}$.
uv: $\lambda_{max}^{pH\ 7\ buffer}$ 255 nm ($\epsilon$, 31600), 310 nm ($\epsilon$, 13000).

EXAMPLE 23

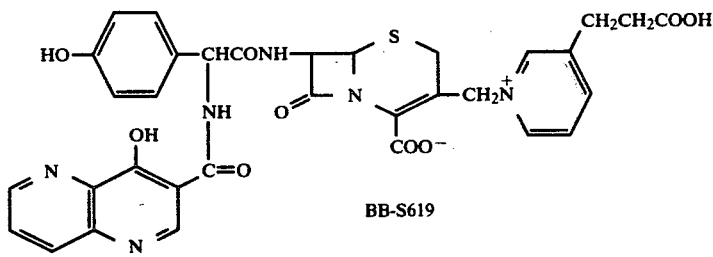

BB-S619

7-[D-α-(4-Hydroxy-1,5-naphthyridine-3-carboxamido)-α-(4-hydroxyphenyl)acetamido]-3-[3-(2-carboxyethylpyridinium]methyl-3-cephem-4-carboxylate, (BB-S619)

Sodium 7-[D-α-(4-hydroxy-1,5-naphthyridine-3-carboxamido)-α-(4-hydroxyphenyl)acetamido]cephalosporanate (BB-S550, 616 mg., 1 m.mole) and KSCN (2.4 g., 25 m.moles) were added to a solution of 2-(3-pyridyl)propionic acid (604 mg., 4 m.moles) in water (2 ml.) containing NaHCO$_3$ (336 mg., 4 m.moles). The mixture was kept standing overnight at 50–52° C. and chromatographed on a column of HP-20 (90 ml.). Elution with 30% aqueous MeOH and evaporation of the eluate gave 190 mg. of solid which was rechromatographed on an HP-20 (30 ml.) column to yield 50 mg. (7%) of the title compound. M. p. 295° C. (grad. dec.).
ir: $\nu_{max}^{KBr}$ 3400, 3250, 1765, 1650, 1610, 1510 cm$^{-1}$.
uv: $\lambda_{max}^{pH\ 7\ Buffer}$ 255 nm ($\epsilon$, 36000), 310 nm ($\epsilon$, 8800).

EXAMPLE 24

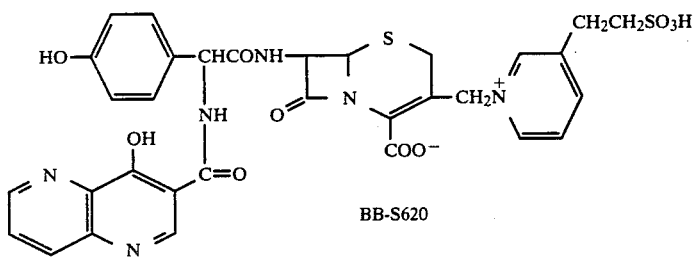

BB-S620

(a) 3-(2-Hydroxyethyl)pyridine

To a solution of ethyl 3-pyridylacetate (1.65 g., 10 m.moles) in methanol (MeOH) (20 ml.) was added NaBH$_4$ (3.87 g., 100 m.moles) at 0°–10° C. over a period of 30 minutes. The mixture was refluxed for three hours, diluted with water (15 ml.) and evaporated to remove the MeOH under reduced pressure. The aqueous residue was extracted with CHCl$_3$ (5×20 ml.). The CHCl$_3$ extracts were combined, dried over MgSO$_4$ and evaporated to dryness to afford 1.2 g. (100%) of 3-(2-hydroxyethyl) pyridine.

ir: $\nu_{max}^{film}$ 3300, 1590, 1570, 1040 cm$^{-1}$. nmr: $\delta_{ppm}^{CDCl_3}$ 2.78 (2H, t, J=6 Hz, CH$_2$), 3.78 (2H, t, J=6 Hz, CH$_2$), 3.76 (1H, m, disappeared by D$_2$O, OH), 7.13 (1H, m, Py-H-5), 7.33 (1H, m, Py-H-4), 8.27 (2H, m, Py-H-2 and H-6).

(b) 3-(2-Chloroethyl)pyridine

A mixture of 3-(2-hydroxyethyl)pyridine (1.2 g., 9.8 m.moles) and thionyl chloride (10 ml.) was refluxed for 3 hours and then excess of the thionyl chloride was removed by evaporation. To the residue was added a 5% aqueous solution of Na$_2$CO$_3$ (20 ml.) and the mixture was extracted with chloroform (2×30 ml.). The extracts were combined, dried with anhydrous Na$_2$SO$_4$ and concentrated to dryness to yield 3-(2-chloroethyl)-pyridine, 1.3 g. (98%).

ir: $\nu_{max}^{film}$ 1590, 1580 cm$^{-1}$. nmr: $\delta_{ppm}^{CDCl_3}$ 3.02 (2H, m, CH$_2$), 3.67 (2H, m, CH$_2$), 7.17 (1H, m, Py-H-5), 7.50 (1H, m, Py-H-4), 8.45 (2H, m, Py-H-2 and H-6).

(c) 3-(2-Sulfoethyl)pyridine

A mixture of Na$_2$SO$_3$ (2.7 g., 21 m.moles) and (3-(2-chloroethyl)pyridine (1.2 g., 8.5 m.moles) in water (10 ml.) was heated under reflux overnight with stirring and column chromatographed on IR-120 resin (H$^+$, 100 ml.) by eluting with water. The eluate containing the desired product was collected and concentrated to give colorless plates (1.1 g., 69%), melting at 275°–278° C.

ir: $\nu_{max}^{nujol}$ 1630, 1020 cm$^{-1}$. nmr: $\delta_{ppm}^{D_2O}$ 3.25 (4H, s, CH$_2$CH$_2$—), 8.00 (1H, m, Py-H-5), 8.62 (3H, m, Py-H-2, H-4 and H-6).

(d)

7-[D-α-(4-Hydroxy-1,5-naphthyridine-3-carboxamido)-α-(4-hydroxyphenyl)acetamido]-3-[3-(2-sulfoethyl)-pyridinium]methyl 3-cephem-4-carboxylate, (BB-S620).

A mixture of sodium 7-[D-α-(4-hydroxy-1,5-naphthyridine-3-carboxamido)-α-(4-hydroxyphenyl)acetamido]cephalosporanate (BB-S550, 616 mg., 1 m.mole), 3-(2-sulfoethyl)pyridine (561 mg., 3m.moles), NaHCO$_3$ (252 mg., 3 m.moles) and KSCN (2.4 g., 25 m.moles) was kept at 50°–52° C. overnight and passed through a column of HP-20 (90ml.). The column was eluted successively with water, 30% aq. MeOH and 50% aq. MeOH. From the 30% aq. MeOH eluate 164 mg. of solid was obtained. The solid was dissolved in 5 ml. of water, adjusted to pH 3 and rechromatographed on an HP-20 column by eluting with 30% aqueous MeOH. The aq. MeOH eluate was concentrated under reduced pressure and lyophilized to give 42 mg. (6%) of the title compound, BB-S620, melting at >250° C. (gradual decomposition).

ir: $\nu_{max}^{KBr}$ 3400, 3250, 1765, 1650, 1610, 1520, 1040 cm$^{-1}$. uv: $\lambda_{max}^{pH\ 7\ Buffer}$ 255 nm (ε, 33300), 310 nm (ε, 8700).

EXAMPLE 25

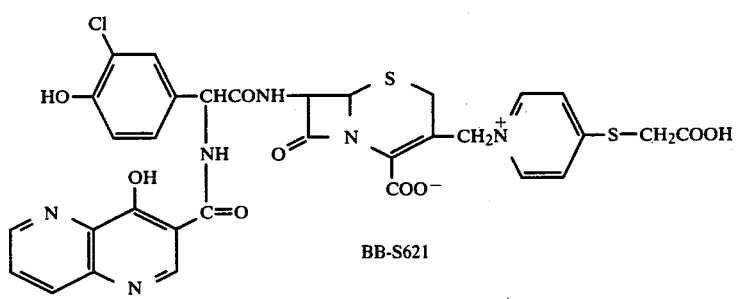

BB-S621

7-[D-α-(4-Hydroxy-1,5-naphthyridine-3-carboxamido)-α-(3-chloro-4-hydroxyphenyl)acetamido]-3-[4-(carboxymethylthio)-pyridinium]methyl-3-cephem-4-carboxylate, (BB-S621)

To a solution of (4-pyridylthio)acetic acid (670 mg., 4m.moles) and NaHCO$_3$ (336 mg., 4m.moles) in 2 ml. of water, sodium 7-[D-α-(4-hydroxy-1,5, -naphthyridine-3-carboxamido)-α-(3-chloro-4-hydroxyphenyl)acetamido]cephalosporanate (650 mg., 1 m.mole) and KSCN (2.4 g., 25 m.moles) were added. The mixture was kept standing at room temperature overnight and passed through a column of HP-20 (90 ml.) eluting with 1 L of water, 0.4 L of 30% aqueous MeOH and 0.5 L of 50% aqueous MeOH successively. The eluate was collected in 20 ml. fractions and monitored by tlc (CH$_3$CN:H$_2$O=4:1, detected with I$_2$). The fractions 55–59 were combined, concentrated to a small volume under reduced pressure and lyophilized to yield 214 mg. (28%) of BB-S621. M.p. >210° C. (gradual decomposition).

ir: $\nu_{max}^{KBR}$ 3400, 3250, 1765, 1650, 1610, 1530 cm$^{-1}$.
uv: $\epsilon_{max}^{pH\ 7\ buffer}$ 255 nm ($\epsilon$, 37000), 310 nm ($\epsilon$, 20000).

EXAMPLE 26

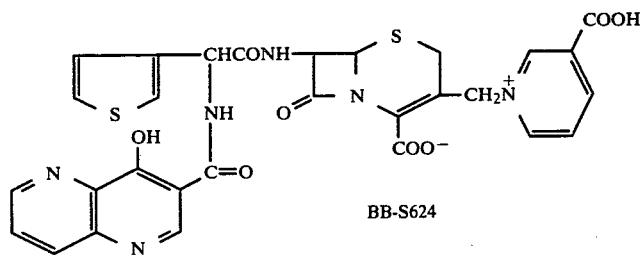

BB-S624

7-[D-α-(4-Hydroxy-1,5-naphthyridine-3-carboxamido)-α-(3-thienyl)acetamido]-3-(3-carboxypyridinium)methyl-3-cephem-4-carboxylate, (BB-S624)

A mixture of sodium 7-[D-α-(4-hydroxy-1,5-naphthyridine-3-carboxamido)-60-(3-thienyl)acetamido]-cephalosporanate (500 mg., 0.83 m.mole), nicotinic acid (406 mg., 3.3 m.moles), NaHCO$_3$ (279 mg., 3.3 m.moles) and KSCN (2 g., 21 m.moles) in 2 ml. water was stirred at 50°–52° C. overnight. The reaction mixture was diluted with 10 ml. of water and chromatographed on a column of HP-20 (90 ml.) eluting with 30% aqueous methanol to afford 110 mg. (20%) of the title compound. M.p. >195° C. (gradual decomposition).

ir: $\nu_{max}^{KBr}$ 3400, 3250, 1765, 1650, 1610, 1520 cm$^{-1}$.
uv: $\lambda_{max}^{pH\ 7\ Buffer}$ 255 nm ($\epsilon$, 35200), 310 nm ($\epsilon$, 9100).

EXAMPLE 27

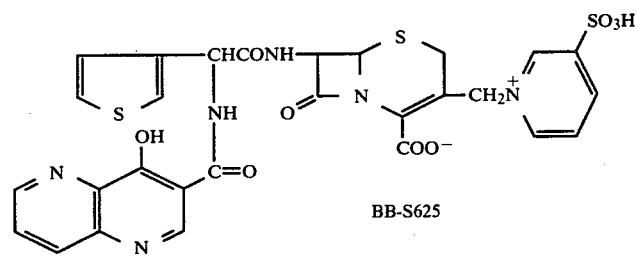

BB-S625

7-[D-α-(4-Hydroxy-1.5-naphthyridine-3-carboxamido)-α-(3-thienyl)acetamido]-3-(3-sulfopyridinium)methyl-3-cephem-4-carboxylate, (BB-S625).

A mixture of 3-sulfopyridine sodium salt dihydrate (716 mg., 3.3 m.moles), sodium 7-[D-α-(4-hydroxy-1,5-naphthyridine-3-carboxamido)-α-(3-thienyl)acetamido]cephalosporanate, (500 mg., 0.83 0.83 m.mole) and KSCN (2.2 g., 23 m.moles) in 2 ml. of water was heated to 52° C. and kept standing at the same temperature. The reaction mixture diluted with 5 ml. of water was chromatographed on a column of HP-20 (90 ml.) which was eluted with 600 ml. of water, 600 ml. of 30% aqueous MeOH and 400 ml. of 50% aqueous MeOH. Evaporation of the 30% aqueous MeOH fractions followed by lyophilization gave 86 mg. (15%) of BB-S625. M.p. >260° C. (gradual decomposition).

ir: $\nu_{max}^{KBr}$ 3400, 3250, 1765, 1655, 1610, 1520, 1040 cm$^{-1}$. uv: $\lambda_{max}^{pH\ 7\ Buffer}$ 255 nm ($\epsilon$, 36000), 310 nm ($\epsilon$, 9100).

EXAMPLE 28

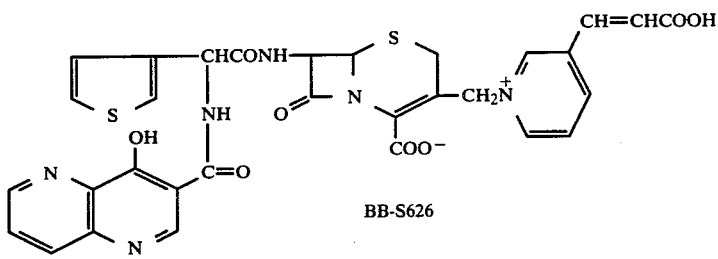

BB-S626

7-[D-α-(4-Hydroxy-1,5-naphthyridine-3-carboxamido)-α-(3-thienyl)acetamido]-3-[3-(2-carboxyvinyl)pyridinium]methyl-3-cephem-4-carboxylate, (BB-S626)

Sodium 7-[D-α-(4-hydroxy-1,5-naphthyridine-3-carboxamido)-α-(3-thienyl)acetamido]cephalosporanate (500 mg., 0.83 m.mole) was added to a mixture of 3-(3- pyridyl)acrylic acid (492 mg., 3.3 m.moles), NaHCO$_3$ (279 mg., 3.3 m.moles) and KSCN (2 g., 21 m.moles) in 2 ml. of water. The mixture was kept standing overnight at 50–52° C. Chromatography on HP-20 by eluting with 30% aqueous MeOH gave 94 mg. (16%) of the title compound. M.p. >295° C. (gradual decomposition).

ir: $\nu_{max}^{KBr}$ 3400, 3200, 1765, 1650, 1610, 1530 cm$^{-1}$.
uv: $\lambda_{max}^{pH\ 7\ Buffer}$ 255 nm ($\epsilon$, 39400), 310 nm ($\epsilon$, 10000).

EXAMPLE 29

7-[D-α-(4-Hydroxy-1,5-naphthyridine-3-carboxamido)-α-(3,4-dihydroxyphenyl)acetamido]-3-(3-sulfopyridinium)methyl-3-cephem-4-carboxylate, 7-[D-α-(4-hydroxy-1,5-naphthyridine-3-carboxamido)-α-(3-chloro-4-hydroxyphenyl)acetamido]-3-(3-sulfopyridinum)methyl-3-cephem-4-carboxylate, 7-[D-α-(4-hydroxy-1,5-naphthyridine-3-carboxamido)-α-(3-methyl-4-hydroxyphenyl)acetamido]-3-(3-sulfopyridinium)methyl-3-cephem-4-carboxylate and 7-[D-α-(4-hydroxy-1,5-naphthyridine-3-carboxamido)-6α-(3-methoxy-4-hydroxyphenyl)acetamido]-3-(3-sulfopyridinium)methyl-3-cephem-4-carboxylate respectively are prepared by substitution in the procedure of Example 6 for the 7-[D-α-amino-α-(4-hydroxyphenyl)acetamido]cephalosproranic acid used therein of an equimolar weight of 7-[D-α-amino-α-(3,4-dihydroxyphenyl)acetamido]cephalosporanic acid, 7[D-α-amino-α-(3-chloro-4-hydroxyphenyl)acetamido]cephalosporanic acid, 7-[D-α-amino-α-(3-methyl-4-hydroxyphenyl)acetamido]cephalosporanic acid and 7-[D-α-amino-α-(3-methoxy-4-hydroxyphenyl)-acetamiido]cephalosporanic acid respectively.

EXAMPLE 30

7-[D-α-(4-Hydroxy-1,5-naphthyridine-3-carboxamido)-α-(3,4-dihydroxyphenyl)acetamido]-3-[3-(2-carboxyvinyl)pyridinium]methyl-3-cephem-4-carboxylate, 7-[D-α-(4-hydroxy-1,5-naphthyridine-3-carboxamido)-α-(3-chloro-4-hydroxyphenyl)- acetamido]-3-[3-(2-carboxyvinyl)pyridinium]methyl-3-cephem 4-carboxylate, 7-[D-α-(4-hydroxy-1,5-naphthyridine-3-carboxamido)-α-(3-methyl-4-hydroxyphenyl)acetamido]-3-]3-(2 (2-carboxyvinyl)pyridinium]methyl-3-cephem-4-carboxylate and 7-]D-α-(4-hydroxy-1,5-naphthyridine-3-carboxamido)-α-(3-methoxy-4-hydroxyphenyl)acetamido]-3-]3-(2-carboxyvinyl)-pyridinium]methyl-3-cephem-4-carboxylate respectively are prepared by substitution in the procedure of Example 8 for the 7-[D-α-amino-α-(4-hydroxyphenyl)acetamido]cephalosporanic acid used therein of an equimolar weight of 7-[D-α-amino-α-(3,4-dihydroxyphenyl)acetamido]cephalosporanic acid, 7-[D-α-amino-α-(3-chloro-4-hydroxyphenyl)acetamido]cephalosporanic acid, 7-[D-α-amino-α-(3-methyl-4-hydroxyphenyl)acetamido]cephalosporanic acid and 7-[D-α-amino-α-(3-methoxy-4-hydroxyphenyl)-acetamido]cephalosporanic acid, respectively.

EXAMPLE 31

7-[D-α-(4-Hydroxy-1,5-naphthyridine-3-carboxamido)-α-(3,4-dihydroxyphenyl)acetamido]-3-(4-carboxymethylthiopyridinium) methyl-3-cephem-4-carboxylate, 7-[D-α-(4-hydroxy-1,5-naphthyridine-3-carboxamido)-α-(3-chloro-4-hydroxyphenyl)-acetamido]-3-(4-carboxymethylthiopyridinium)methyl-3-cephem-4-carboxylate, 7-[D-α-(4-hydroxy-1,5-naphthyridine-3-carboxamido)-α-(3-methyl-4-hydroxyphenyl)acetamido]-3-(4-carboxymethylthiopyridinium)methyl-3-cephem-4-carboxylate and 7-[D-α-(4-hydroxy-1,5-naphthyridine-3-carboxamido)-α-(3-methoxy-4-hydroxyphenyl)acetamido]-3-(4carboxymethylthiopyridinium)-methyl-3-cephem-4-carboxylate respectively are prepared by substitution in the procedure of Example 11 for the 7-[D-α-amino-α-(4-hydroxyphenyl)acetamido]cephalosporanic acid used therein of an equimolar weight of 7-[D-α-amino-α-(3,4-dihydroxyphenyl) acetamido]cephalosporanic acid, 7-[D-α-amino-α(3-chloro-4-hydroxyphenyl)acetamido]cephalosporanic acid, 7-[D-α-amino-α-(3-methyl-4-hydroxyphenyl)acetamido]cephalosporanic acid and 7-[D-α-amino-α-(3-methoxy-4-hydroxyphenyl)acetamido]-cephalosporanic acid, respectively.

EXAMPLE 32

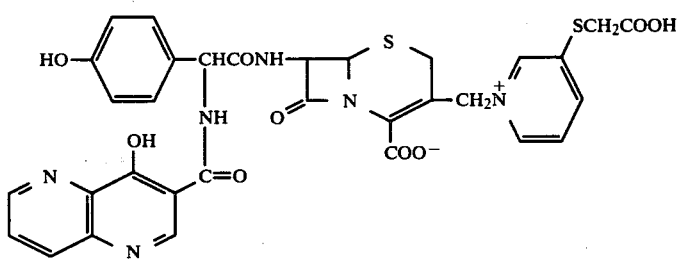

7-[D-α-(4-Hydroxy-1,5-naphthyridine-3-carboxamido)-α-(4-hydroxyphenyl)acetamido]-3-(3-carboxymethylthiopyridinium)-methyl-3-cephem-4-carboxylate According to a procedure similar to Example 1 the title compound is prepared from sodium 7-[D-α-(4-hydroxy-1,5-naphthyridine-3-carboxamido)-α-(4-hydroxyphenyl)acetamido]-cephalosporanate (617 mg., 1 m.mole), (3-pyridylthio)acetic acid (670 mg., 4 m.moles) and KSCN (2.4 g., 25 m.moles) and converted to the sodium salt.

EXAMPLE 33

7-[D-α-(4-Hydroxy-1,5-naphthyridine-3-carboxamido)-α-(3,4-dihydroxyphenyl)acetamido]-3-(3-carboxymethylthiopyridinium)methyl-3-cephem-4-carboxylate, 7-[D-α-(4-hydroxy-1,5-naphthyridine-3-carboxamido)-α-(3-chloro-4-hydroxyphenyl)-acetamido]-3-(3-carboxymethylthiopyridinium)methyl-3-cephem-4-carboxylate, 7-[D-α-(4-hydroxy-1,5-naphthyridine-3-carboxamido)-α-(3-methyl-4-hydroxyphenyl)acetamido]-3-(3-carboxy-methylthiopyridinium)methyl-3-cephem-4-carboxylate and 7-[D-α-(4-hydroxy-1,5-naphthyridine-3-carboxamido)-α-(3-methoxy-4-hydroxyphenyl)acetamido]-3-(3-carboxymethylthiopyridinium)-methyl-3-cephem-4-carboxylate respectively are prepared by substitution in the procedure of Example 32 for the 7-[D-α-amino-α-(4-hydroxyphenyl)acetamido]cephalosporanic acid used therein of an equimolar weight of 7-[D-α-amino-α-(3,4-dihydroxyphenyl)-acetamido]cephalosporanic acid, 7-[D-α-amino-α-(3-chloro-4-hydroxyphenyl)acetamido]cephalosporanic acid, 7-[D-α-amino-α-(3-methyl-4-hydroxyphenyl)acetamido]cephalosporanic acid and 7-[D-α-amino-α-(3-methoxy-4-hydroxyphenyl)acetamido]cephalosporanic acid, respectively.

EXAMPLE 34

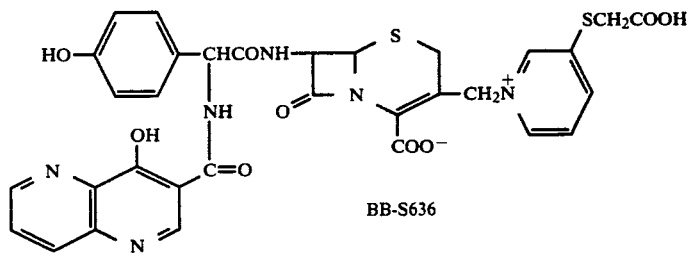

BB-S636

7-[D-α-(4-Hydroxy-1,5-naphthyridine-3-carboxamido)-α-(4-hydroxyphenyl)acetamido]-3-(3-carboxymethylthiopyridinium)-methyl-3-cephem-4-carboxylate, (BB-S636)

A mixture of sodium 7-[D-α-(4-hydroxy-1,5-naphthyridine-3-carboxamido)-α-(4-hydroxyphenyl)acetamido]cephalosporanate[(1)] (616 mg., 1 m.mole), 3-pyridylthioacetic acid[(2)] (507 mg., 3 m.moles), NaHCO$_3$ (252 mg., 3 m.moles) and KSCN (2.4 g., 25 m.moles) in 2 ml. of water was kept standing overnight at 50°-52° C. The mixture was column-chromatographed on HP-20 eluting with 30% aqueous methanol to afford 230 mg. (32% yield) of the desired compound. M.p. >220° C. (gradually decomposed.)
[(1)]Japan Kokai 51-32576 (3/19/76, Sumitomo).
[(2)]U.S. Pat. No. 2,544,904 (3/13/51, Hoffmann-LaRoche).

ir: $\nu_{max}^{KBr}$ 3400, 3200, 1765, 1650, 1610, 1520 cm$^{-1}$.
uv: $\lambda_{max}^{pH\ 7\ Buffer}$ 255 nm ($\epsilon$, 39000); 310 nm ($\epsilon$, 10000).

EXAMPLE 35

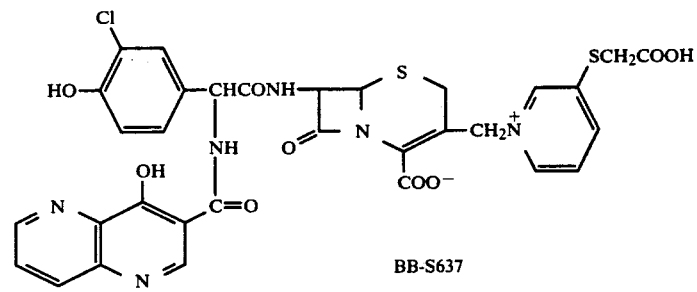

BB-S637

7-[D-α-(4-Hydroxy-1,5-naphthyridine-3-carboxamido)-α-(3-chloro-4-hydroxyphenyl)acetamido]-3-(3-carboxymethylthiopyridinium)methyl-3-cephem-4-carboxylate, (BB-S637)

Pyrid-3-ylthioacetic acid (507 mg., 3.7 m.moles) and NaHCO$_3$ (320 mg., 3.7 m.moles) were added to a solution of sodium 7-[D-α-(4-hydroxy-1,5-naphthyridine-3-carboxamido)-α-(3-chloro-4-hydroxyphenyl)acetamido]cephalosporanate (600 mg., 0.92 m.mole) and KSCN (2.2 g., 23 m.moles) in 2 ml. of water and the mixture was kept standing overnight at 50°-52° C. The reaction mixture was chromatographed on a column of HP-20 (90 ml.) eluting with 30% aqueous methanol to afford 160 mg. (21%) of the title compound. M.p. >240° C. (gradually decomposed).

ir: $\nu_{max}^{KBr}$ 3400, 3250, 1760, 1650, 1610, 1520 cm$^{-1}$.
uv: $\lambda_{max}^{pH\ 7\ Buffer}$ 255 nm ($\epsilon$, 38000), 310 nm ($\epsilon$, 11000).

EXAMPLE 36

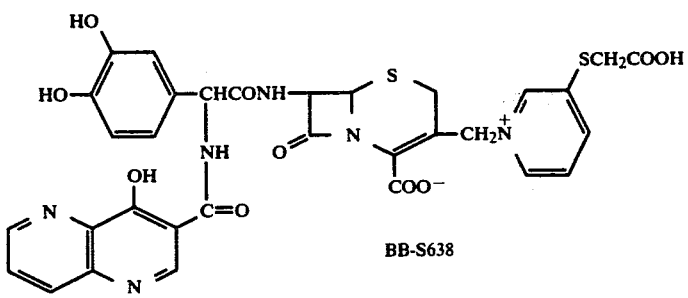

BB-S638

7-[D-α-(4-Hydroxy-1,5-naphthyridine-3-carboxamido)-α-(3,4-dihydroxyphenyl)acetamido]-3-(3-carboxymethylthiopyridinium)-methyl-3-cephem-4-carboxylate, (BB-S638)

A mixture of 3-pyridylthioacetic acid (507 mg., 3 m.moles), NaHCO$_3$ (252 mg., 3 m.moles), sodium 7-[D-α-(4-hydroxy-1,5-naphthyridine-3-carboxamido)-α-

(3,4-dihydroxyphenyl)-acetamido]cephalosporanate (633 mg., 1 m.mole) and KSCN (2.4 g., 25 m.moles) was stirred at 50°-52° C. for 1 hour and kept standing at the same temperature overnight. The reaction mixture was column-chromatographed on HP-20 (90 ml.) by eluting with water, 10%- and 30%-aqueous methanol successively. The desired product was obtained from the fractions of aqueous methanol eluate. Yield 270 mg. (36%). M.p. >240° C. (gradually decomposed).

ir: $\nu_{max}^{KBr}$ 3250, 1760, 1640, 1610, 1520 cm$^{-1}$. uv: $\lambda_{max}^{pH\ 7\ Buffer}$ 255 nm ($\epsilon$, 33000), 310 nm ($\epsilon$, 9700).

EXAMPLE 37

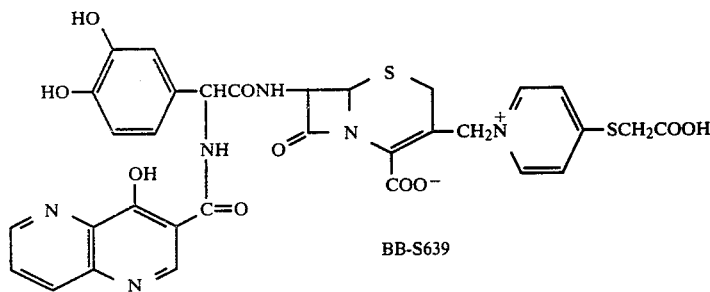

BB-S639

7-[D-α-(4-Hydroxy-1,5-naphthyridine-3-carboxamido)-α-(3,4-dihydroxyphenyl)acetamido]-3-(4-carboxymethylthiopyridinium)-methyl-3-cephem-4-carboxylate, (BB-S639)

A mixture of 4-pyridylthioacetic acid (507 mg., 3 m.moles), NaHCO₃ (252 mg., 3 m.moles), KSCN (2.4 g., 25 m.moles) and sodium 7-[D-α-(4-hydroxy-1,5-naphthyridine-3-carboxamido)-α-(3,4-dihydroxyphenyl)acetamido]cephalosporanate (633 mg., 1 m.mole) in 2 ml. of water was slurried with stirring and allowed to stand overnight at 50°-52° C. Isolation of the product was carried out by HP-20 column chromatography. Elution was performed by using water (0.7 L), 10% aqueous methanol (0.2 L) and 30% aqueous methanol (1 L) successively. The eluate was collected in 20-ml. fractions monitoring with tlc (silica-gel, CH₃CN/H₂O=4/1, detected with I₂). The fractions containing the desired product were collected, concentrated to a small volume in vacuo and lyophilized to afford the title compound. Yield 245 mg. (33%). M.p. 255° C. (gradually decomposed).

ir: $\nu_{max}^{KBr}$ 3250, 1760, 1640, 1610, 1520 cm$^{-1}$. uv: $\lambda_{max}^{pH\ 7\ Buffer}$ 255 nm ($\epsilon$, 35000), 310 nm ($\epsilon$, 15000).

Results of Biological Testing

In vitro activity

Minimun inhibitory concentrations (MIC) were determined by the serial two-fold agar dilution method using Steers' apparatus on Mueller-Hinton agar plate against 31 test organisms for the primary screening and also against 64 strains of *Pseudomonas aeruginosa* for the secondary evaluation. The results are shown in Table 1 in terms of relative activity with respect to the standard compound CBPC (carbenicillin) which was set at 100%. In each group the calculation was based on the geometric mean of the observed MICs.

TABLE 1

| | In vitro Relative Activity (CBPC = 100%) | | | | |
|---|---|---|---|---|---|
| | Primary Evaluation* | | | | Secondary Pseudomonas aeruginosa (61-64) % |
| Compound No. | Gp (6) % | Gn-I (13) % | Gn-II (6) % | Ps (6) % | |
| BB-S579 | 28 | 230 | 22 | 2880 | 2780 |
| BB-S580 | 27 | 359 | 33 | 2490 | 1780 |
| BB-S584 | 22 | 166 | 14 | 725 | 1180 |
| BB-S585 | 20 | 53 | 4 | 297 | 466 |
| BB-S586 | 6 | 88 | 11 | 362 | 351 |
| BB-S587 | 28 | 166 | 16 | 2378 | 3380 |
| Lot 2 | 56 | 87 | 19 | 3200 | 3570 |
| BB-S588 | 45 | 350 | 45 | 1767 | 2030 |
| BB-S589 | 56 | 146 | 14 | 1449 | 1880 |
| Lot 2 | 45 | 107 | 44 | 2900 | 2970 |
| BB-S591 | 31 | 167 | 18 | 883 | 1160 |
| BB-S592 | 56 | 121 | 11 | 594 | 695 |
| BB-S599 | 35 | 260 | 83 | 2180 | 2010 |
| BB-S600 | 70 | 107 | 30 | 2340 | 2500 |
| BB-S601 | 79 | 107 | 25 | 3200 | 2490 |
| BB-S602 | 58 | 94 | 63 | 2080 | 1530 |
| BB-S603 | 73 | 80 | 38 | 1150 | 1270 |
| BB-S604 | 50 | 94 | 45 | 1450 | 2030 |
| BB-S605 | 40 | 83 | 40 | 1310 | 1300 |
| BB-S606 | 45 | 16 | 11 | 656 | 624 |
| BB-S607 | 35 | 24 | 13 | 883 | 695 |
| BB-S608 | 13 | 53 | 14 | 975 | 1207 |
| BB-S609 | 18 | 53 | 11 | 1450 | 1375 |
| BB-S610 | 16 | 57 | 14 | 656 | 491 |
| BB-S619 | 31 | 88 | 18 | 725 | 1600 |
| BB-S620 | 28 | 60 | 14 | 800 | 1800 |
| BB-S621 | 20 | 121 | 18 | 800 | 1400 |
| BB-S624 | 79 | 47 | 10 | 328 | 413 |
| BB-S625 | 50 | 32 | 7 | 200 | 400 |
| BB-S626 | 45 | 41 | 11 | 231 | 460 |
| BB-S636 | 71 | 242 | 50 | 7070 | |
| BB-S637 | 71 | 113 | 25 | 3530 | |
| BB-S638 | 8 | 69 | 8 | 2380 | |
| BB-S639 | 20 | 242 | 35 | 4310 | |

*GP = *S. aureus* (6 strains);
Gn-I = *E. coli* (9), Klebsiella sp. (2), *Pr. mirabilis* (1), *Sal. enteritidis* (1);
Gn-II = *Ent. cloacae* (3), *Pr. vulgaris* (1), *Pr. morganii* (1), *S. marcescens* (1);
Ps. = *Ps. aeruginosa* (6).

In vivo Activity

The in vivo efficacy was evaluated by intramuscular treatment against three kinds of experimental infection in mice.

The in vivo tests were carried out using the following three pathogenic organisms:

*Pseudomonas aeruginosa* A9843
*Escherichia coli* Juhl
*Staphylococcus aureus* Smith Mice were challenged intraperitoneally with approximately a 100×LD₅₀ dose of the pathogens in a 5% mucin suspension. The mice were treated with test compound by I.M. route immediately after the bacterial challenge. A group of five mice were used for each dosage level and the animals were observed for 5 days to determine the median protective dose (PD₅₀). The results are summarized in Table 2.

TABLE 2

| | PD$_{50}$ (Mice, I.M.) | | |
|---|---|---|---|
| Compound No. | Staphylococcus aureus Smith mg./kg. | Escherichia coli Juhl mg./kg. | Pseudomonas aeruginosa A9843 mg./kg. |
| BB-S579 | 2 | 1.8 | 6.4 |
| BB-S580 | 2.6 | 1.2 | 6.4 |
| BB-S584 | 7.6 | 4.2 | 36 |
| BB-S585 | 10 | 7.4 | 86 |
| BB-S587 | | | 3.13 |
| Lot 2 | 3.7 | 2.4 | 2.2 |
| BB-S588 | 5 | 1.56 | 6.8 |
| BB-S589 | | | 4 |
| Lot 2 | 3.7 | 1.9 | 3.2 |
| BB-S591 | 6.15 | 6.25 | 12.5 |
| BB-S592 | 4.6 | 6.25 | 38 |
| BB-S599 | 2.2 | 2.4 | 8.4 |
| BB-S600 | 2 | 2.2 | 6.2 |
| BB-S601 | | | 4.4 |
| BB-S602 | 0.8 | 1.4 | 8.4 |
| BB-S603 | 1.15 | 2.2 | 18 |
| BB-S604 | 2.5 | 2.4 | 6.2 |
| BB-S605 | 3.1 | 3.1 | 8.4 |
| BB-S606 | 4.2 | | 25 |
| BB-S607 | 4.5 | | 23 |
| BB-S608 | 8.5 | 1.4 | 2.4 |
| BB-S609 | 17 | 1.8 | 1.2 |
| BB-S610 | 17 | 1.8 | 2.8 |
| BB-S619 | | 3.2 | 4.6 |
| BB-S620 | | 3.2 | 6.25 |
| BB-S621 | | 2.4 | 4.6 |
| BB-S624 | | | 20 |
| BB-S625 | | | 36 |
| BB-S626 | | | 30 |

Antibiotic blood levels were determined in mice following intramuscular administration of the test compounds at 20 mg./kg. The blood samples were collected from the orbital sinuses into heparinized capillary tubes at 15, 30, 60 and 120 minutes after administration. The antibiotic concentration was determined by the paper disc-agar diffusion method using *Escherichia coli* NIHJ as the assay organism. The results are shown in Table 3.

TABLE 3

| | Blood Level (I.M., 20 mg./kg.) | |
|---|---|---|
| Compound No. | Peak Concentration mcg./ml. | Half-life min. |
| BB-S579 | 12 | 75 |
| BB-S580 | 16.5 | 33 |
| BB-S584 | 12.5 | 81 |
| BB-S585 | 5.8 | 60 |
| BB-S587 | 3 | 40 |
| BB-S588 | 4.4 | 59 |
| BB-S589 | 7 | 60 |
| BB-S591 | 11 | 54 |
| BB-S592 | 12 | 55 |
| BB-S599 | 7.8 | 54 |
| BB-S600 | 6.2 | 70 |
| BB-S601 | 10 | 70 |
| BB-S602 | 8 | 60 |
| BB-S603 | 9 | 44 |
| BB-S604 | 10.5 | 56 |
| BB-S605 | 9.4 | 54 |
| BB-S606 | 11 | 55 |
| BB-S607 | 10 | 60 |
| BB-S608 | 8.5 | 50 |
| BB-S609 | 7.4 | 51 |
| BB-S610 | 6.2 | 60 |
| BB-S619 | 10 | 55 |
| BB-S620 | 12.5 | 40 |
| BB-S621 | 10 | 54 |

TABLE 3-continued

| | Blood Level (I.M., 20 mg./kg.) | |
|---|---|---|
| Compound No. | Peak Concentration mcg./ml. | Half-life min. |
| BB-S624 | 9.5 | 50 |
| BB-S625 | 10 | 54 |
| BB-S626 | 8.8 | 42 |

Preparation of Starting Materials

Sodium 7-[D-α-(4-hydroxy-1,5-naphthyridine-3-carboxamido)-α-phenylacetamido]cephalosporanate. (1)

The N-hydroxysuccinimido ester of 4-hydroxy-1,5-naphthyridine-3-carboxylic acid (950 mg., 3.3 m.moles) was added to a solution of the TFA (trifluoroacetic acid) salt of cephaloglycin (1.56 g., 3 m.moles) and 1.3 ml. (9.3 m.moles) of Et₃N in 15 ml. of DMF (dimethylformamide). The mixture was stirred overnight at room temperature and evaporated under reduced pressure. The residue was triturated with 20 ml. of dry acetone, filtered and dissolved in 4 ml. of DMF. To the solution was added 6 ml. of 1 M sodium 2-ethylhexanoate in AcOEt (ethyl acetate) solution and the mixture was stirred for 15 minutes, concentrated to a small volume under reduced pressure and diluted with 100 ml. of acetone. The resulting precipitate was dissolved in 5 ml. of water and chromatographed on a column of HP-20 resin (90 ml.). The column was developed successively with water (300 ml.) and 30% aqueous methanol (500 ml.) (MeOH).

The eluates were collected in 20-ml. fractions, monitoring with uv (260 nm) and tlc (silica-gel plate, CH₃CN:H₂O=4:1, detected with I₂, Rf=0.3). The fractions 15–53 were collected by filtration and dried to afford 620 mg. (34%) of sodium 7-[D-α-(4-hydroxy-1,5-naphthyridine-3-carboxamido)-α-phenylacetamido]-cephalosporanate (1), melting at >300° C.

ir: $\nu_{max}^{KBr}$ 3450, 3300, 1765, 1650, 1610, 1530 cm$^{-1}$.
uv: $\lambda_{max}^{pH\ 7\ Buffer}$ 255 nm (ε, 35000), 295 nm (ε, 8200), 310 nm (ε, 8800), 325 nm (ε, 6500).

Anal. calcd. for C₂₇H₂₂N₅O₈SNa.3H₂O: C, 49.62; H, 4.32, N, 10.71; S, 4.91. Found: C, 49.47; H, 3.69; N, 10.86; S, 5.07.

Sodium 7-[D-α-(4-hydroxy-1,5-naphthyridine-3-carboxamido)-α-(4-hydroxyphenyl)acetamido]cephalosporanate. (3)

The N-hydroxysuccinimido ester of 4-hydroxy-1,5-naphthyridine-3-carboxylic acid (1.7 g., 6 m.moles) was added to a solution of the TFA salt of 7-[D-α-amino-α-(4-hydroxyphenyl) acetamido]cephalosporanic acid (2.7 g., 5 m.moles) in 20 ml. of DMF and 2.2 ml. (16 m.moles) of Et₃N. The mixture was stirred overnight at room temperature and concentrated to a small volume under reduced pressure. The residue was triturated with 20 ml. of dry acetone, filtered and dissolved in 10 ml. of DMF. To the solution was added 10 ml. of 1 M sodium 2-ethylhexanoate in AcOEt. The mixture was stirred for 15 minutes, evaporated to a small volume and diluted with 50 ml. of acetone to separate the precipitate which was dissolved in 15 ml. of water and chromatographed on a column of HP-20 (250 ml.). The column was developed successively with water (1 L) and 30% aqueous MeOH (2 L). The eluates were collected in 20-ml. fractions monitoring with uv (260 nm) and tlc (silica-gel plate, CH$_3$CN:H$_2$O=4:1, detected with I$_2$, Rf=0.2). The fractions 52–105 were combined and concentrated to a small volume under reduced pressure. The residue was diluted with 100 ml. of dry acetone to separate the precipitate which was collected by filtration and dried to afford 1.81 g. (59%) of sodium 7-[D-α-(4-hydroxy-1,5-naphthyridine-3-carboxamido)-α-(4-hydroxyphenyl)acetamido]cephalosporanate (3) melting at >300° C.

ir: $\nu_{max}^{KBr}$ 3450, 3210, 1765, 1650, 1610, 1530, 1520 cm$^{-1}$. uv: $\lambda_{max}^{pH\ 7\ Buffer}$ 225 nm (ε, 28000), 256 nm (ε, 37000), 310 nm (ε, 9600).

Anal. calcd. for C$_{27}$H$_{22}$N$_5$O$_9$SNa.3H$_2$O: C, 48.43; H, 4.21; N, 10.46; S, 4.79. Found: C, 47.93; H, 3.68; N, 10.12; S, 4.64.

Sodium 7-[D-α-(4-hydroxy-1,5-naphthyridine-3-carboxamido)-α-(3,4-dihydroxyphenyl)acetamido]cephalosporanate. (5)

The N-hydroxysuccinimido ester of 4-hydroxy-1,5-naphthyridine-3-carboxylic acid (1 g., 2.6 m.moles) was added to a solution of the TFA salt of 7-[D-α-amino-α-(3,4-dihydroxyphenyl)acetamido]cephalosporanic acid (1 g., 1.8 m.moles) (Farmdoc 22850W; Japan Kokai 50-82086; U.K. Pat. No. 1,472,174) and 1 ml. (7.2 m.moles) of Et$_3$N in 15 ml. of DMF. The mixture was stirred overnight at room temperature and concentrated to a small volume under reduced pressure. The concentrate was triturated with 20 ml. of dry acetone, filtered and dissolved in 5 ml. of DMF. To the solution was added sodium 2-ethylhexanoate in AcOEt (1 M solution, 6.3 ml.). The mixture was stirred for 15 minutes, concentrated to a small volume and diluted with 150 ml. of acetone to separate the precipitate which was dissolved in 15 ml. of water and chromatographed on a column of HP-20 (90 ml.). The column was developed successively with water (1 L) and 30% aqueous MeOH (1 L). The eluate was collected in 20-ml. fractions monitoring with uv (260 nm) and tlc (silica gel plate, CH$_3$CN:H$_2$O=4:1, detected with I$_2$, Rf=0.18). Fractions 51–57 were combined and concentrated in vacuo. The concentrate was diluted with 50 ml. of dry acetone to separate the precipitate which was collected by filtration and dried to afford 310 mg. (28%) of 5, melting at 300° C.

ir: $\nu_{max}^{KBr}$ 3400, 3250, 1760, 1660, 1530 cm$^{-1}$. uv: $\lambda_{max}^{pH\ 7\ Buffer}$ 255 nm (ε, 16600), 275 nm (ε, 9500), 310 nm (ε, 4500).

Anal. Calcd. for C$_{27}$H$_{22}$N$_5$O$_{10}$SNa.3H$_2$O: C, 47.30; H, 4.12; N, 10.21; S, 4.68. Found: C, 46.93; H, 4.23; N, 9.98; S, 5.94.

Sodium 7-[D-α-(4-hydroxy-1,5-naphthyridine-3-carboxamido)-α-(3-chloro-4-hydroxyphenyl)acetamido]cephalosporanate. (7)

The N-hydroxysuccinimido ester of 4-hydroxy-1,5-naphthyridine-3-carboxylic acid (565 mg., 1.97 m.moles) was added to a solution of the TFA salt of 7-[D-α-amino-α-(3-chloro-4-hydroxyphenyl)acetamido]cephalosporanic acid (930 mg., 1.64 m.moles) (U.S. Pat. No. 3,489,751) and 0.74 ml. (5.3 m.moles) of Et$_3$N in 10 ml. of DMF. The mixture was stirred overnight at room temperature and concentrated to a small volume under reduced pressure. The concentrate was triturated with 30 ml. of dry acetone, filtered and dissolved in 5 ml. of DMF. To the solution was added 2 ml. of 1 M sodium 2-ethylhexanoate in AcOEt solution. The mixture was stirred for 15 minutes, evaporated to a small volume and diluted with 50 ml. of acetone to separate the precipitate (1.1 g.) which was dissolved in 10 ml. of water and chromatographed on a column of HP-20 (90 ml.). The column was developed successively with water (400 ml.) and 30% aqueous MeOH (1 L). The eluate was collected in 20-ml. fractions monitoring with tlc (silica gel plate, CH$_3$CN:H$_2$O=4:1 detected with I$_2$, Rf=0.2). Fractions 22–37 were combined and concentrated to a small volume in vacuo. The residue was diluted with 50 ml. of dry acetone to separate the precipitate which was collected by filtration and dried to afford 620 mg. (58%) of the desired compound 7 melting at >300° C.

ir: $\nu_{max}^{KBr}$ 3400, 3250, 1765, 1650, 1610, 1570, 1530 cm$^{-1}$. uv: $\lambda_{max}^{1\%\ NaHCO_3}$ 262 nm (ε, 44000), 310 nm (ε, 10000).

Sodium 7-[D-α-(4-hydroxy-1,5-naphthyridine-3-carboxamido)-α-(3-thienyl)acetamido]cephalosporanate. (9)

The N-hydroxysuccinimido ester of 4-hydroxy-1,5-naphthyridine-3-carboxylic acid (714 mg., 2.5 m.moles) was added to a solution of the TFA salt of 7-[D-α-amino-α-(3-thienyl)acetamido]cephalosporanic acid (1.09 g., 2.07 m.moles) and 0.93 ml. (6.6 m.moles) of Et$_3$N in 10 ml. of DMF. The mixture was stirred overnight at room temperature and concentrated to a small volume under reduced pressure. The residue was triturated with 30 ml. of acetone, filtered and dissolved in 5 ml. of DMF. To the solution was added 2 ml. of 1 M sodium 2-ethylhexanoate in AcOEt solution. The mixture was evaporated to a small volume and diluted with 50 ml. of acetone to separate the precipitate (1.3 g.) which was dissolved in 10 ml. of water and chromatographed on a column of HP-20 (90 ml.). The column was developed successively with water (800 ml.) and 30% aqueous MeOH (1 L). The eluate was collected in 20-ml. fractions monitoring with tlc (silica gel, CH$_3$CN:H$_2$O=4:1, detected with I$_2$, Rf=0.4). Fractions 43–59 were combined and concentrated to a small volume in vacuo. The residue was diluted with 100 ml. of dry acetone to separate the precipitate which was collected by filtration and dried to afford 680 mg. (54%) of the desired compound 9 melting at >300° C.

$\nu_{max}^{KBr}$ 3400, 3250, 1765, 1650, 1610, 1570, 1530 cm$^{-1}$. uv: $\lambda_{max}^{pH\ 7\ Buffer}$ 255 nm (ε, 36000), 310 nm (ε, 9100).

Anal. Calcd. for C$_{25}$H$_{20}$N$_5$O$_8$S$_2$Na.2H$_2$O: C, 46.80; H, 3.77; N, 10.92; S, 9.99. Found: C, 46.24; H, 3.33; N, 10.86; S, 9.54.

Other starting materials are prepared from known 7-[D-α-amino-α-(substituted aryl)acetamidocephalosporanic acids] by the procedures illustrated above.

The presently preferred species of the present invention are the compounds of Example 8 (BB-S589), Example 11 (BB-S599), Example 6 (BB-S587) and Example 34 (BB-S636).

Another preferred group of the compounds of the present invention consists of the compounds having the D configuration in the 7-sidechain and the formula

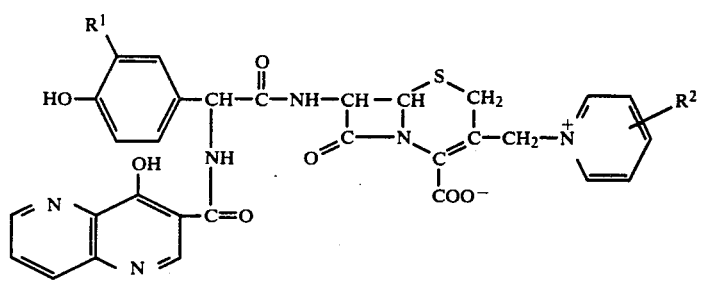

wherein $R^1$ is hydrogen, hydroxy or chloro and $R^2$ is 3- or 4-$CH_2COOH$, 3- or 4-$SO_3H$, 3- or 4-$CH_2CH_2COOH$, 3- or 4-$CH=CHCOOH$, 3- or 4-$CH_2CH_2SO_3H$ or 3- or 4-$SCH_2COOH$ or an alkali metal salt thereof.

A preferred group of the compounds of the present invention consists of the compounds having the D configuration in the 7-sidechain and the formula

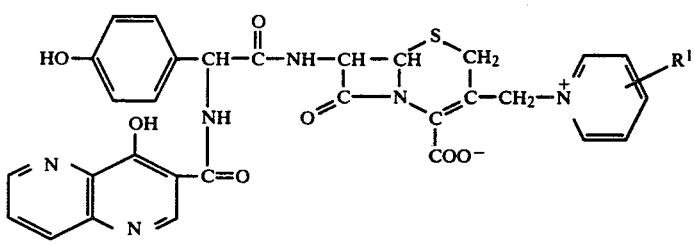

wherein $R^1$ is 3- or 4-$CH_2COOH$, 3- or 4-$SO_3H$, 3- or 4-$CH_2CH_2COOH$, 3- or 4-$CH=CHCOOH$, 3- or 4-$CH_2CH_2SO_3H$ or 3- or 4-$SCH_2COOH$ or an alkali metal salt thereof.

A particularly preferred series of compounds within the present invention are the compounds having the D configuration in the 7-sidechain and the formula

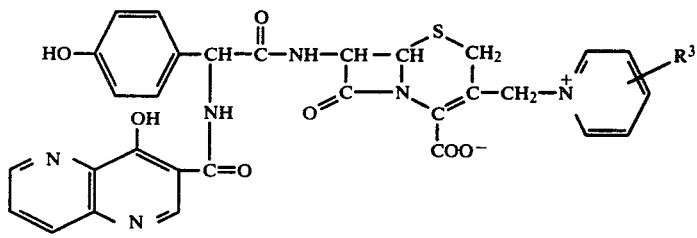

wherein $R^3$ is 3- or 4-$SO_3H$, 3- or 4-$CH_2CH_2COOH$, 3- or 4-$CH=CHCOOH$, 3- or 4-$CH_2CH_2SO_3H$ or 3- or 4-$SCH_2COOH$ or an alkali metal salt thereof.

This invention is capable of industrial application.

We claim:

1. A compound having the D configuration in the 7-sidechain and the formula

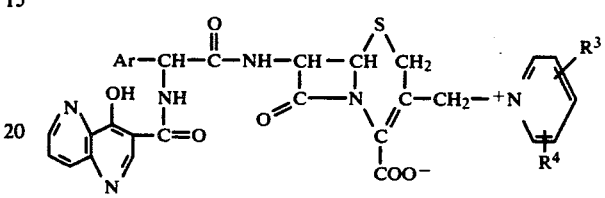

wherein
$R^1$ is hydrogen or hydroxy and $R^2$ is hydrogen, hydroxy, methyl, methoxy or chloro and $R^3$ is hydrogen and $R^4$ is carboxyl, carboxymethyl, —$SO_3H$, —$CH_2CH_2COOH$, —$CH=CHCOOH$, —$CH_2CH_2SO_3H$, —$SCH_2COOH$ or
$R^3$ and $R^4$ are each carboxyl substituted at the 2,3-, 2,4-, 2,5-, 2,6-, 3,4- or 3,5-positions or an alkali metal salt thereof.

2. A compound having the D configuration in the 7-sidechain and the formula

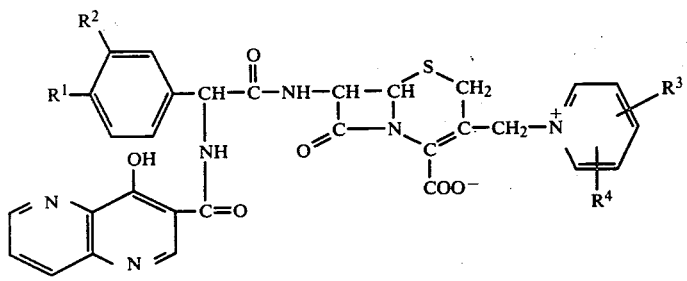

wherein
R¹ is hydrogen or hydroxy and R² is hydrogen, hydroxy, methyl, methoxy or chloro and R³ is hydrogen and R⁴ is carboxyl, carboxymethyl, —SO₃H, —CH₂CH₂COOH, —CH=CHCOOH, —CH₂CH₂SO₃H, —SCH₂COOH or R³ and R⁴ are each carboxyl substituted at the 2,3-, 2,4-, 2,5-, 2,6-, 3,4- or 3,5-positions or an alkali metal salt thereof.

3. A compound having the D configuration in the 7-sidechain and the formula

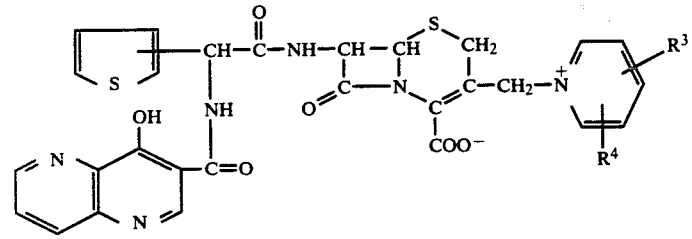

wherein
R³ is hydrogen and R⁴ is carboxyl, carboxymethyl, —SO₃H, —CH₂CH₂COOH, —CH=CHCOOH, —CH₂CH₂SO₃H, —SCH₂COOH or R³ and R⁴ are each carboxyl substituted at the 2,3-, 2,4-, 2,5-, 2,6-, 3,4- or 3,5-positions or an alkali metal salt thereof.

4. A compound having the D configuration in the 7-sidechain and the formula

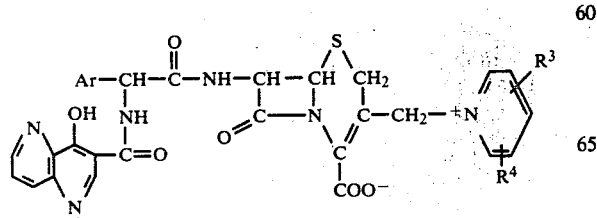

wherein Ar is 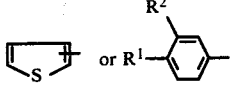

wherein
R¹ is hydrogen or hydroxy and R² is hydrogen, hydroxy, methyl, methoxy or chloro and R³ is hydrogen and R⁴ is carboxyl, carboxymethyl, 3- or 4-SO₃H, 3- or 4-CH₂CH₂COOH, 3- or 4-CH=CHCOOH, 3- or 4-CH₂CH₂SO₃H or 3- or 4-SCH₂COOH or R³ and R⁴ are each carboxyl substituted at the 2,3-, 2,4-, 2,5-, 2,6-, 3,4- or 3,5-positions or an alkali metal salt thereof.

5. A compound having the D configuration in the 7-sidechain and the formula

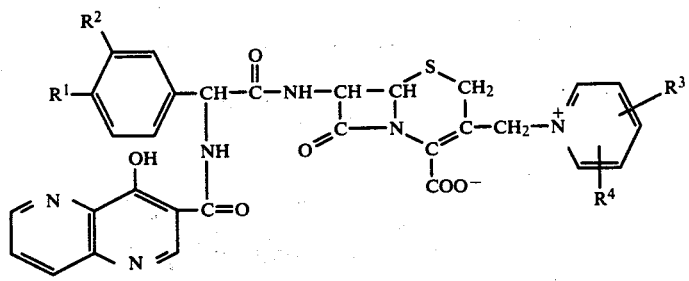

wherein
R¹ is hydrogen or hydroxy and R² is hydrogen, hydroxy, methyl, methoxy or chloro and R³ is hydrogen and R⁴ is carboxyl, carboxymethyl, 3- or 4-SO₃H, 3- or 4-CH₂CH₂COOH, 3- or 4-CH=CHCOOH, 3- or 4-CH₂CH₂SO₃H or 3- or 4-SCH₂COOH or R³ and R⁴ are each carboxyl substituted at the 2,3-, 2,4-, 2,5-, 2,6-, 3,4- or 3,5-positions or an alkali metal salt thereof.

6. A compound having the D configuration in the 7-sidechain and the formula

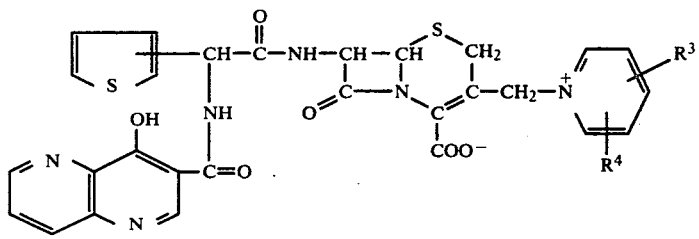

wherein
- R³ is hydrogen and R⁴ is carboxyl, carboxymethyl, 3- or 4-SO₃H, 3- or 4-CH₂CH₂COOH, 3- or 4-CH=CHCOOH, 3- or 4-CH₂CH₂SO₃H or 3- or 4-SCH₂COOH or
- R³ and R⁴ are each carboxyl substituted at the 2,3-, 2,4-, 2,5-, 2,6-, 3,4- or 3,5-positions or an alkali metal salt thereof.

7. A compound having the D configuration in the 7-sidechain and the formula

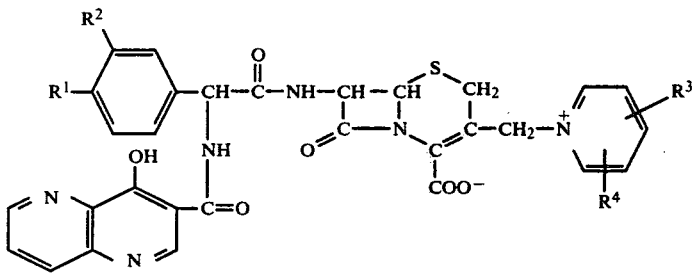

wherein
- R¹ is hydrogen or hydroxy and R² is hydrogen, hydroxy or chloro and R³ is hydrogen and R⁴ is carboxyl, carboxymethyl, 3- or 4-SO₃H, 3- or 4-CH₂CH₂COOH, 3- or 4-CH=CHCOOH, 3- or 4-CH₂CH₂SO₃H or 3- or 4-SCH₂COOH or
- R³ and R⁴ are each carboxyl substituted at the 2,3-, 2,4-, 2,5-, 2,6-, 3,4- or 3,5-positions or an alkali metal salt thereof.

8. The compound of claim 4 which is 7-[D-α-(4-hydroxyl-1,5-naphthyridine-3-carboxamido)-α-phenylacetamido]-3-(4′-carboxypyridinium)methyl-3-cephem-4-carboxylate.

9. The compound of claim 4 which is 7-[D-α-(4-hydroxy-1,5-naphthyridine-3-carboxamido)-α-(4-hydroxyphenyl)-acetamido]-3-(4′-carboxypyridinium)-methyl-3-cephem-4-carboxylate.

10. The compound of claim 4 which is 7-[D-α-(4-hydroxy-1,5-naphthyridine-3-carboxamido)-α-(3,4-dihydroxyphenyl)acetamido]-3-(4′-carboxypyridinium)methyl-3-cephem-4-carboxylate.

11. The compound of claim 4 which is 7-[D-α-(4-hydroxy-1,5-naphthyridine-3-carboxamido)-α-(3-chloro-4-hydroxyphenyl)acetamido]-3-(4′-carboxypyridinium)methyl-3-cephem-4-carboxylate.

12. The compound of claim 3 which is 7-[D-α-(4-hydroxy-1,5-naphthyridine-3-carboxamido)-α-(3-thienyl)-acetamido]-3-(4′-carboxypyridinium)methyl-3-cephem-4-carboxylate.

13. The compound of claim 4 which is 7-[D-α-(4-hydroxy-1,5-naphthyridine-3-carboxamido)-α-phenylacetamido]-3-(3′-carboxymethylpyridinium)-methyl-3-cephem-4-carboxylate.

14. The compound of claim 4 which is 7-[D-α-(4-hydroxy-1,5-naphthyridine-3-carboxamido)-α-(4-hydroxyphenyl)-acetamido]-3-(3′-carboxymethylpyridinium)methyl-3-cephem-4-carboxylate.

15. The compound of claim 4 which is 7-[D-α-(4-hydroxy-1,5-naphthyridine-3-carboxamido)-α-(3,4-dihydroxyphenyl)acetamido]-3-(3′-carboxymethylpyridinium)methyl-3-cephem-4-carboxylate.

16. The compound of claim 4 which is 7-[D-α-(4-hydroxy-1,5-naphthyridine-3-carboxamido)-α-(3-chloro-4-hydroxyphenyl)acetamido]-3-(3′-carboxymethylpyridinium)methyl-3-cephem-4-carboxylate.

17. The compound of claim 3 which is 7-[D-α-(4-hydroxy-1,5-naphthyridine-3-carboxamido)-α-(3-thienyl)-acetamido]-3-(3′-carboxymethylpyridinium)-methyl-3-cephem-4-carboxylate.

18. The compound of claim 4 which is 7-[D-α-(4-hydroxy-1,5-naphthyridine-3-carboxamido)-α-phenylacetamido]-3-(4′-carboxymethylpyridinium)-methyl-3-cephem-4-carboxylate.

19. The compound of claim 4 which is 7-[D-α-(4-hydroxy-1,5-naphthyridine-3-carboxamido)-α-(4-hydroxyphenyl)-acetamido]-3-(4′-carboxymethylpyridinium)methyl-3-cephem-4-carboxylate.

20. The compound of claim 4 which is 7-[D-α-(4-hydroxy-1,5-naphthyridine-3-carboxamido)-α-(3,4-dihydroxyphenyl)acetamido]-3-(4′-carboxymethylpyridinium)methyl-3-cephem-4-carboxylate.

21. The compound of claim 4 which is 7-[D-α-(4-hydroxy-1,5-naphthyridine-3-carboxamido)-α-(3-chloro-4-hydroxyphenyl)acetamido]-3-(4′-carboxymethylpyridinium)methyl-3-cephem-4-carboxylate.

22. The compound of claim 3 which is 7-[D-α-(4-hydroxy-1,5-naphthyridine-3-carboxamido)-α-(3-thienyl)-acetamido]-3-(4′-carboxymethylpyridinium)-methyl-3-cephem-4-carboxylate.

23. The compound of claim 4 which is 7-[D-α-(4-hydroxy-1,5-naphthyridine-3-carboxamido)-α-phenylacetamido]-3-(3′-sulfopyridinium)methyl-3-cephem-4-carboxylate.

24. The compound 7-[D-α-(4-hydroxy-1,5-naphthyridine-3-carboxamido)-α-(4-hydroxyphenyl)-acetamido]-3-(3′-sulfopyridinium)methyl-3-cephem-4-carboxylate.

25. The compound of claim 4 which is 7-[D-α-(4-hydroxy-1,5-naphthyridine-3-carboxamido)-α-(3,4-dihydroxyphenyl)acetamido]-3-(3'-sulfopyridinium)-methyl-3-cephem-4-carboxylate.

26. The compound of claim 4 which is 7-[D-α-(4-hydroxy-1,5-naphthyridine-3-carboxamido)-α-(3-chloro-4-hydroxyphenyl)acetamido]-3-(3'-sulfopyridinium)methyl-3-cephem-4-carboxylate.

27. The compound of claim 3 which is 7-[D-α-(4-hydroxy-1,5-naphthyridine-3-carboxamido)-α-(3-thienyl)-acetamido]-3-(3'-sulfopyridinium)methyl-3-cephem-4-carboxylate.

28. The compound of claim 4 which is 7-[D-α-(4-hydroxy-1,5-naphthyridine-3-carboxamido)-α-phenylacetamido]-3-(3'-carboxypyridinium)methyl-3-cephem-4-carboxylate.

29. The compound of claim 4 which is 7-[D-α-(4-hydroxy-1,5-naphthyridine-3-carboxamido)-α-(4-hydroxyphenyl)-acetamido]-3-(3'-carboxypyridinium)-methyl-3-cephem-4-carboxylate.

30. The compound of claim 4 which is 7-[D-α-(4-hydroxy-1,5-naphthyridine-3-carboxamido)-α-(3,4-dihydroxyphenyl)acetamido]-3-(3'-carboxypyridinium)methyl-3-cephem-4-carboxylate.

31. The compound of claim 4 which is 7-[D-α-(4-hydroxy-1,5-naphthyridine-3-carboxamido)-α-(3-chloro-4-hydroxyphenyl)acetamido]-3-(3'-carboxypyridinium)methyl-3-cephem-4-carboxylate.

32. The compound of claim 3 which is 7-[D-α-(4-hydroxy-1,5-naphthyridine-3-carboxamido)-α-(3-thienyl)-acetamido]-3-(3'-carboxypyridinium)methyl-3-cephem-4-carboxylate.

33. The compound of claim 4 which is 7-[D-α-(4-hydroxy-1,5-naphthyridine-3-carboxamido)-α-phenylacetamido]-3-(2'-carboxypyridinium)methyl-3-cephem-4-carboxylate.

34. The compound of claim 4 which is 7-[D-α-(4-hydroxy-1,5-naphthyridine-3-carboxamido)-α-(4-hydroxyphenyl)-acetamido]-3-(2'-carboxypyridinium)-methyl-3-cephem-4-carboxylate.

35. The compound of claim 4 which is 7-[D-α-(4-hydroxy-1,5-naphthyridine-3-carboxamido)-α-(3,4-dihydroxyphenyl)acetamido]-3-(2'-carboxypyridinium)methyl-3-cephem-4-carboxylate.

36. The compound of claim 4 which is 7-[D-α-(4-hydroxy-1,5-naphthyridine-3-carboxamido)-α-(3-chloro-4-hydroxyphenyl)acetamido]-3-(2'-carboxypyridinium)methyl-3-cephem-4-carboxylate.

37. The compound of claim 3 which is 7-[D-α-(4-hydroxy-1,5-naphthyridine-3-carboxamido)-α-(3-thienyl)-acetamido]-3-(2'-carboxypyridinium)methyl-3-cephem-4-carboxylate.

38. The compound of claim 4 which is 7-[D-α-(4-hydroxy-1,5-naphthyridine-3-carboxamido)-α-phenylacetamido]-3-(4'-sulfoethylpyridinium)methyl-3-cephem-4-carboxylate.

39. The compound of claim 4 which is 7-[D-α-(4-hydroxy-1,5-naphthyridine-3-carboxamido)-α-(4-hydroxyphenyl)-acetamido]-3-(4'-sulfoethylpyridinium)methyl-3-cephem-4-carboxylate.

40. The compound of claim 4 which is 7-[D-α-(4-hydroxy-1,5-naphthyridine-3-carboxamido)-α-(3,4-dihydroxyphenyl)acetamido]-3-(4'-sulfoethylpyridinium)methyl-3-cephem-4-carboxylate.

41. The compound of claim 4 which is 7-[D-α-(4-hydroxy-1,5-naphthyridine-3-carboxamido)-α-(3-chloro-4-hydroxyphenyl)acetamido]-3-(4'-sulfoethylpyridinium)methyl-3-cephem-4-carboxylate.

42. The compound of claim 3 which is 7-[D-α-(4-hydroxy-1,5-naphthyridine-3-carboxamido)-α-(3-thienyl)-acetamido]-3-(4'-sulfoethylpyridinium)methyl-3-cephem-4-carboxylate.

43. The compound of claim 4 which is 7-[D-α-(4-hydroxy-1,5-naphthyridine-3-carboxamido)-α-phenylacetamido]-3-[3'-(2-carboxyvinyl)pyridinium]-methyl-3-cephem-4-carboxylate.

44. The compound 7-[D-α-(4-hydroxy-1,5-naphthyridine-3-carboxamido)-α-(4-hydroxyphenyl)acetamido]-3-[3'-(2-carboxyvinyl)pyridinium]methyl-3-cephem-4-carboxylate.

45. The compound of claim 4 which is 7-[D-α-(4-hydroxy-1,5-naphthyridine-3-carboxamido)-α-(3,4-dihydroxyphenyl)acetamido]-3-[3'-(2-carboxyvinyl)-pyridinium]methyl-3-cephem-4-carboxylate.

46. The compound of claim 4 which is 7-[D-α-(4-hydroxy-1,5-naphthyridine-3-carboxamido)-α-(3-chloro-4-hydroxyphenyl)acetamido]-3-[3'-(2-carboxyvinyl)pyridinium]-methyl-3-cephem-4-carboxylate.

47. The compound of claim 3 which is 7-[D-α-(4-hydroxy-1,5-naphthyridine-3-carboxamido)-α-(3-thienyl)-acetamido]-3-[3'-(2-carboxyvinyl)pyridinium]-methyl-3-cephem-4-carboxylate.

48. The compound of claim 4 which is 7-[D-α-(4-hydroxy-1,5-naphthyridine-3-carboxamido)-α-phenylacetamido]-3-(4'-carboxymethylthiopyridinium)-methyl-3-cephem-4-carboxylate.

49. The compound 7-[D-α-(4-hydroxy-1,5-naphthyridine-3-carboxamido)-α-(4-hydroxyphenyl)acetamido]-3-(4'-carboxymethylthiopyridinium)methyl-3-cephem-4-carboxylate.

50. The compound of claim 4 which is 7-[D-α-(4-hydroxy-1,5-naphthyridine-3-carboxamido)-α-(3,4-dihydroxyphenyl)acetamido]-3-(3'-sulfoethylpyridinium)methyl-3-cephem-4-carboxylate.

51. The compound of claim 4 which is 7-[D-α-(4-hydroxy-1,5-naphthyridine-3-carboxamido)-α-(3-chloro-4-hydroxyphenyl)acetamido]-3-(3'-sulfoethylpyridinium)methyl-3-cephem-4-carboxylate.

52. The compound of claim 4 which is 7-[D-α-(4-hydroxy-1,5-naphthyridine-3-carboxamido)-α-(4-hydroxyphenyl)-acetamido]-3-(2-carboxyethylpyridinium)methyl-3-cephem-4-carboxylate.

53. The compound of claim 4 which is 7-[D-α-(4-hydroxy-1,5-naphthyridine-3-carboxamido)-α-(4-hydroxyphenyl)-acetamido]-3-[3'-(2-sulfoethyl)-pyridinium]methyl-3-cephem-4-carboxylate.

54. The compound of claim 4 which is 7-[D-α-(4-hydroxy-1,5-naphthyridine-3-carboxamido)-α-(3,4-dihydroxyphenyl)acetamido]-3-(4'-carboxymethylthiopyridinium)methyl-3-cephem-4-carboxylate.

55. The compound 7-[D-α-(4-hydroxy-1,5-naphthyridine-3-carboxamido)-α-(3-chloro-4-hydroxyphenyl)acetamido]-3-(4'-carboxymethylthiopyridinium)methyl-3-cephem-4-carboxylate.

56. The compound of claim 4 which is 7-[D-α-(4-hydroxy-1,5-naphthyridine-3-carboxamido)-α-phenylacetamido]-3-(3'-carboxymethylthiopyridinium)-methyl-3-cephem-4-carboxylate.

57. The compound 7-[D-α-(4-hydroxy-1,5-naphthyridine-3-carboxamido)-α-(4-hydroxyphenyl)-acetamido]-3-(3'-carboxymethylthiopyridinium)methyl-3-cephem-4-carboxylate.

58. The compound of claim 4 which is 7-[D-α-(4-hydroxy-1,5-naphthyridine-3-carboxamido)-α-(3,4-dihydroxyphenyl)acetamido]-3-(3'-carboxymethylthiopyridinium)methyl-3-cephem-4-carboxylate.

59. The compound of claim 4 which is 7-[D-α-(4-hydroxy-1,5-naphthyridine-3-carboxamido)-α-(3-chloro-4-hydroxyphenyl)acetamido]-3-(3′-carboxymethylthiopyridinium)methyl-3-cephem-4-carboxylate.

60. A compound having the D configuration in the 7-sidechain and the formula

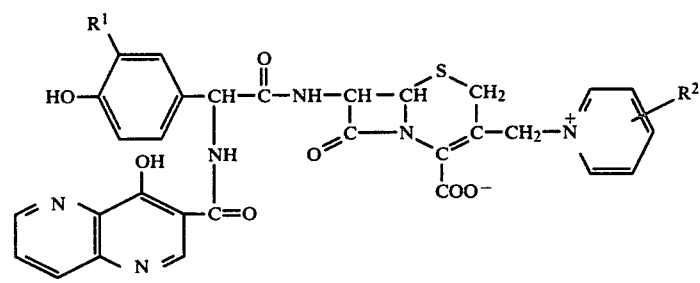

wherein $R^1$ is hydrogen, hydroxy or chloro and $R^2$ is 3- or 4-$CH_2COOH$, 3- or 4-$SO_3H$, 3- or 4-$CH_2CH_2COOH$, 3- or 4-$CH=CHCOOH$, 3- or 4-$CH_2CH_2SO_3H$ or 3- or 4-$SCH_2COOH$ or an alkali metal salt thereof.

61. A compound having the D configuration in the 7-sidechain and the formula

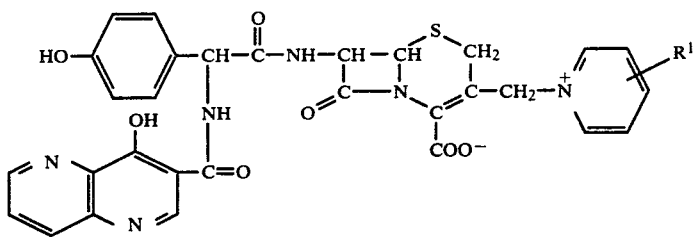

wherein $R^1$ is 3- or 4-$CH_2COOH$, 3- or 4-$SO_3H$, 3- or 4-$CH_2CH_2COOH$, 3- or 4-$CH=CHCOOH$, 3- or 4-$CH_2CH_2SO_3H$ or 3- or 4-$SCH_2COOH$ or an alkali metal salt thereof.

62. A compound having the D configuration in the 7-sidechain and the formula

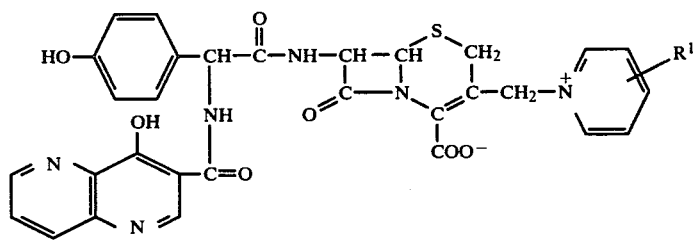

wherein $R^1$ is 3- or 4-$SO_3H$, 3- or 4-$CH_2CH_2COOH$, 3- or 4-$CH=CHCOOH$, 3- or 4-$CH_2CH_2SO_3H$ or 3- or 4-$SCH_2COOH$ or an alkali metal salt thereof.

* * * * *